(12) United States Patent
Wilson et al.

(10) Patent No.: US 11,458,338 B2
(45) Date of Patent: Oct. 4, 2022

(54) FACIAL SHIELDING SYSTEM FOR PROTECTION FROM ENVIRONMENTAL HAZARDS

(71) Applicants: John Paul Wilson, Huntington, NY (US); Sandra Wilson, Huntington, NY (US)

(72) Inventors: John Paul Wilson, Huntington, NY (US); Sandra Wilson, Huntington, NY (US)

(*) Notice: Subject to any disclaimer, the term of this patent is extended or adjusted under 35 U.S.C. 154(b) by 695 days.

(21) Appl. No.: 15/770,082

(22) PCT Filed: Oct. 25, 2016

(86) PCT No.: PCT/US2016/058703
§ 371 (c)(1),
(2) Date: Apr. 20, 2018

(87) PCT Pub. No.: WO2017/074954
PCT Pub. Date: May 4, 2017

(65) Prior Publication Data
US 2018/0311515 A1    Nov. 1, 2018

Related U.S. Application Data

(60) Provisional application No. 62/246,102, filed on Oct. 25, 2015, provisional application No. 62/246,104, filed on Oct. 25, 2015.

(51) Int. Cl.
*A62B 18/00*    (2006.01)
*A62B 31/00*    (2006.01)
(Continued)

(52) U.S. Cl.
CPC ........ *A62B 18/006* (2013.01); *A41D 13/1107* (2013.01); *A42B 3/20* (2013.01);
(Continued)

(58) Field of Classification Search
CPC ......... A42B 3/226; A62B 18/003; A62B 9/00; A62B 9/06; A62B 18/00; A62B 18/02;
(Continued)

(56) References Cited

U.S. PATENT DOCUMENTS 2,560,215 A * 7/1951 Christensen ......... A62B 18/003
128/200.28
5,353,605 A * 10/1994 Naaman ............. A41D 13/0053
2/171.3
(Continued)

FOREIGN PATENT DOCUMENTS

RU    145879     9/2014
SU    331594     12/1972
(Continued)

OTHER PUBLICATIONS

International Search Report and Written Opinion of international application No. PCT/US16/58703 dated Mar. 6, 2017.
(Continued)

*Primary Examiner* — Victoria Murphy
*Assistant Examiner* — Ned T Heffner
(74) *Attorney, Agent, or Firm* — John Murray; Rimon Law

(57) ABSTRACT

A system which protects the user from electromagnetic radiation, in particular the eyes, face and/or head from UV radiation and/or excessive light as required, while also protecting from thrown particles, projectiles or fluids from striking a user, in particular the eyes, face and/or head, and at the same time providing clean air to breathe.

19 Claims, 11 Drawing Sheets

(51) Int. Cl.
  *A62B 18/02* (2006.01)
  *A41D 13/11* (2006.01)
  *A42B 3/20* (2006.01)
  *A61B 5/00* (2006.01)
  *A61G 5/10* (2006.01)
  *A62B 7/10* (2006.01)
  *A62B 9/00* (2006.01)
  *A62B 18/08* (2006.01)
  *B62B 9/00* (2006.01)

(52) U.S. Cl.
  CPC ............. *A61B 5/6803* (2013.01); *A61G 5/10* (2013.01); *A62B 7/10* (2013.01); *A62B 9/00* (2013.01); *A62B 9/006* (2013.01); *A62B 18/003* (2013.01); *A62B 18/02* (2013.01); *A62B 18/08* (2013.01); *A62B 31/00* (2013.01); *B62B 9/00* (2013.01)

(58) Field of Classification Search
  CPC ..... A62B 18/006; A61M 16/00; A61M 16/10; A61M 16/105
  See application file for complete search history.

(56) References Cited

U.S. PATENT DOCUMENTS

| | | | | |
|---|---|---|---|---|
| 5,413,097 | A * | 5/1995 | Birenheide | A62B 7/10 128/202.22 |
| 5,601,078 | A * | 2/1997 | Schaller | A62B 18/08 128/201.24 |
| 6,826,783 | B1 * | 12/2004 | Grove | A42B 3/10 128/201.25 |
| 7,178,931 | B1 * | 2/2007 | Murphy | A62B 18/08 2/410 |
| 2004/0182394 | A1 * | 9/2004 | Alvey | A62B 7/02 128/205.22 |
| 2005/0011516 | A1 * | 1/2005 | Lukas | A62B 18/006 128/201.24 |
| 2006/0125623 | A1 * | 6/2006 | Appelt | A61B 5/02055 340/521 |
| 2007/0028372 | A1 * | 2/2007 | VanDerWoude | A42B 3/322 2/457 |
| 2008/0023002 | A1 * | 1/2008 | Guelzow | A62B 18/02 128/201.24 |
| 2009/0089908 | A1 * | 4/2009 | Huh | A62B 18/003 2/8.6 |
| 2011/0283431 | A1 * | 11/2011 | Miller, IV | G02C 7/101 2/10 |
| 2012/0051904 | A1 * | 3/2012 | Hagen | B62K 11/02 415/224 |
| 2016/0228670 | A1 * | 8/2016 | Av-Gay | A61M 16/0057 |
| 2017/0113075 | A1 * | 4/2017 | Reiser | A62B 23/02 |

FOREIGN PATENT DOCUMENTS

| | | | |
|---|---|---|---|
| WO | 2009064555 | 5/2009 | |
| WO | WO-2009064555 A1 * | 5/2009 | ............. A42B 3/286 |
| WO | 2014031671 | 2/2014 | |
| WO | 2015036652 | 3/2015 | |
| WO | 2015195496 | 12/2015 | |
| WO | WO-2016018797 A1 * | 2/2016 | ........ A61M 16/0066 |

OTHER PUBLICATIONS

Supplementary European Search Report of Application No. EP 16 86 0630 dated Sep. 30, 2019.

* cited by examiner

FACIAL SHIELDING SYSTEM FOR PROTECTION FROM ENVIRONMENTAL HAZARDS

The present application claims priority from U.S. Application No. 62/246,104 and U.S. Application No. 62/246,102, both filed Oct. 25, 2015, which are incorporated herein by reference.

FIELD

The present application relates generally to the field of facial shielding to provide protection from environmental harms, such as contaminated air, electromagnetic radiation (e.g., ultraviolet radiation) and projected particles or fluids.

BACKGROUND

Many environments including those of modern urban living create conditions in which human beings are bombarded with environmental hazards like contaminated air and projected particles or fluids. This is particularly the case for individuals who routinely travel, such as by foot or bicycle, or who work in outside environments. In addition, such individuals are subject to electromagnetic radiation, such as ultraviolet radiation, in particular during daytime travel and work outside. Consequently, there is a need for a convenient, aesthetically pleasing, comfortable and quick-to-don shielding device that provides protection to the face against such environmental hazards as thrown projectiles or fluids, electromagnetic radiation, including ultraviolet radiation (UV), toxic or noxious material in the air, and poor air quality in general. Prior attempts to address this need have, however, been unable to simultaneously address this broad range of hazards in a convenient and cost-effective and effective manner. The present application provides an effective, energy-saving facial shielding system that protects the face, eyes and mouth against bad air, particulate matter and electromagnetic radiation including UV, while also providing clean air breathing air to the respiratory system. Further aspects and advantages of the application will appear from the following description taken together with the accompanying drawings.

SUMMARY

One aspect of the present application relates to a system for providing air and protection from environmental hazards to a subject in need thereof, comprising: a housing having an air intake and an air exit; an air purification system that receives air that has passed through the air intake of the housing; an air delivery system, preferably flexible, that delivers air that has passed through the air purification system and through the air exit of the housing; a manifold air delivery system that receives air from the air delivery system; a first air supply system that receives air from the manifold air delivery system, wherein the first air supply system comprises one or more apertures that allow directed airflow in a space between a protection pane and a face of the subject, wherein the protection pane is positioned in front of the face of the subject; a second air supply system that receives air from the manifold air delivery system, wherein the second air supply system comprises one or more apertures that allow directed airflow in the space between the protection pane and the face of the subject; and wherein the directed airflow from the apertures of the second air supply system is in an enclosing direction to the directed airflow from apertures of the first air supply system. In a particular embodiment, the housing has an interior that comprises an air propulsion system, an energy storage system or an energy generation system, and control circuitry that controls the air propulsion system, the energy storage system or the energy generation system. In a further embodiment, the air purification system is positioned within the interior of the housing.

Another aspect of the present application relates to a method for providing air and protection from environmental hazards to a subject in need thereof, comprising: pulling air through an air intake of a housing; passing the air through an air purification system; expelling the air through an air exit of the housing and into a flexible air delivery system; feeding air into a manifold air delivery system through the flexible air delivery system; delivering air through the manifold air delivery system into a first air supply system and a second air supply system; positioning the first air supply system and the second air supply system upon a protection pane, wherein the positions of the first and second air supply system do not overlap upon the protection pane; integrating the first air supply system and the second air supply system into the positions on the protection pane; placing the protection pane in front of a face of a subject; directing airflow from the first air supply system over the face of the subject when the protection pane is in front of the face of the subject, wherein one or more apertures in the first air supply system controls the direction of the airflow from the first air supply system; directing airflow from the second air supply system over the face of the subject when the protection pane is in front of the face of the subject, wherein one or more apertures in the second air supply system controls the direction of the airflow from the second air supply system; orientating the apertures of the first and second air supply systems so that the direction of airflow from the second air supply system is in an enclosing direction to the direction of airflow from the first air supply system when the protection pane is in front of the face of the subject.

Another aspect of the present application relates to a device for delivery of purified air to a face of a subject in need thereof, comprising: an air purification system, wherein the air purification system has an attachment via an enclosed space to a manifold air delivery system; a support system that supports the manifold air supply system and connects the manifold air supply system to a protection pane; a first air supply system and a second air supply system that are connected to the protection pane; one or more apertures in the first air supply system that are orientated to direct airflow over the face of the subject when the protection pane is positioned in front of the face of the subject; one or more apertures in the second air supply system that are orientated to direct airflow over the face of the subject when the protection pane is positioned in front of the face of the subject; and wherein the apertures of second air supply system are oriented to direct airflow in an enclosing direction to the airflow from the apertures of the first air supply system; and further wherein the support system, the manifold air supply system, the protection pane and the first air supply system and the second air supply system are integrated to form a single unit. In one embodiment, the protection pane comprises a liquid crystal panel, wherein the liquid crystal panel permits modulatable tuning of the transmission of light from full-or near full transparency to significant light attenuation. In one embodiment, the device is attached to a vehicle, wherein the device is supported by the vehicle, and further wherein the occupant of the vehicle receives the air flow directed by the device. In one embodiment, the vehicle is a stroller or a wheelchair. In one embodiment, wherein the device further comprises a pollution sensor. In one embodiment, the pollution sensor communicates a warning to the subject that pollution levels are elevated above a threshold level. In one embodiment, the air purification system is modified to respond to the detection of elevated pollution levels. In one embodiment, the device comprises an injection system into the airflow provided from a storage system containing additional gases to inject into the airflow. In one embodiment, the device comprises external and/or internal lights controllable manually or automatically to provide lighting during conditions of darkness. In one embodiment, the device comprises at least one or more speakers and microphones, wherein speakers or microphones are either internal or external with respect to the protection pane, or both. In one embodiment, the device comprises ear buds or ear covers. In one embodiment, the device comprises airflow sensors which detect wind flow around the user. In one embodiment, the device comprises a camera fitted internally, wherein the internal camera is user-facing, and/or externally, wherein the external camera is facing the same direction as the user's viewpoint. In one embodiment, the device comprises health sensors selected from the group comprising sensors for the user's temperature, blood pressure, breathing rate, lung capacity, oxygen consumption, $CO_2$ production, heart rate, brain waves, hydration state, skin color, skin conductivity, eye dilation, or eye white color. In one embodiment, the device comprises a dosing device selected from the group comprising a sprayer, vaper, atomizer, vaporizer, inhaler or electrospray device. In one embodiment, the device comprises a wireless communication unit, wherein the wireless communication unit is in communication with other devices worn by subjects. In one embodiment, the device receives communications from other devices regarding pollution, traffic or heat.

BRIEF DESCRIPTION OF THE DRAWINGS

The above and other objects and advantages of the application will be apparent upon consideration of the following detailed description, taken in conjunction with the accompanying figures.

DETAILED DESCRIPTION

Figure 1:
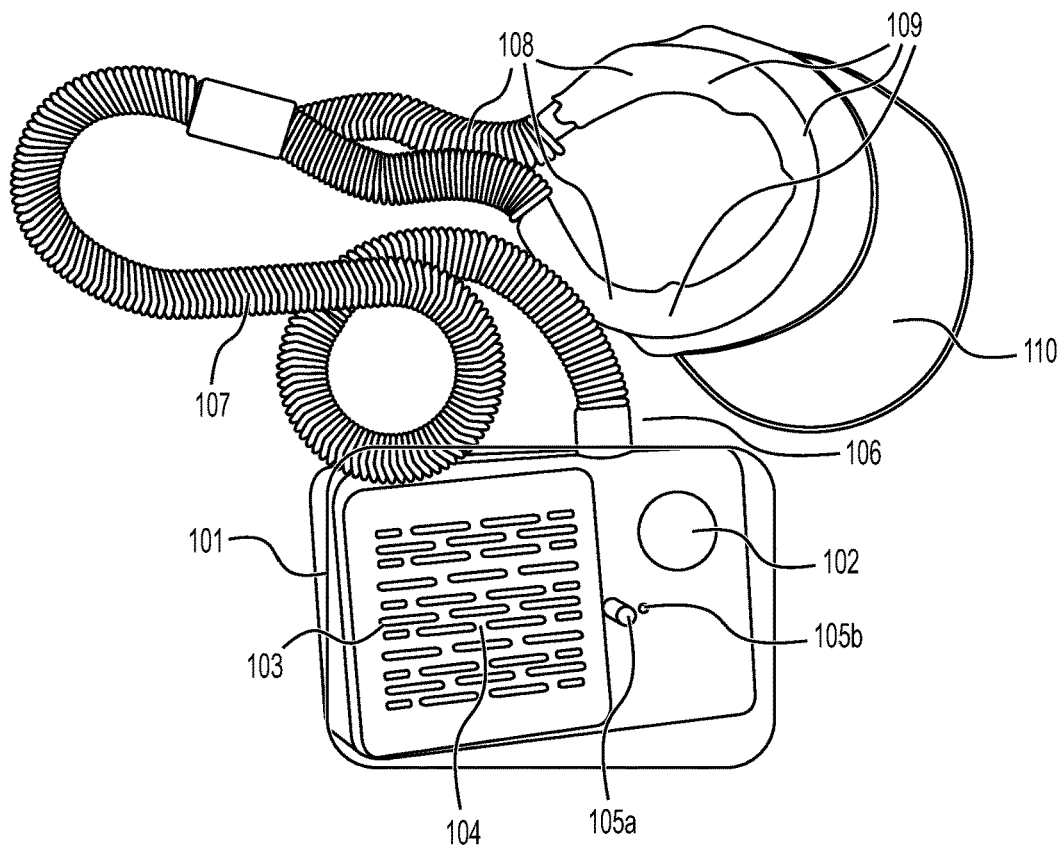
FIG. 1 shows the assembled facial shielding system.

Some modes for carrying out the present invention are presented in terms of its exemplary embodiments, herein discussed below. However, the present invention is not limited to the described embodiment and a person skilled in the art will appreciate that many other embodiments of the present invention are possible without deviating from the basic concept of the present invention, and that any such work around will also fall under the scope of this application. It is envisioned that other styles and configurations of the present invention can be easily incorporated into the teachings of the present invention, and only particular configurations shall be shown and described for purposes of clarity and disclosure and not by way of limitation of scope.

Headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). The terms "a" and "an" herein do not denote a limitation of quantity, but rather denote the presence of at least one of the referenced items. The use of "or" means "and/or" unless stated otherwise or where the use of "and/or" is clearly inappropriate. The use of "a" means "one or more" unless stated otherwise or where the use of "one or more" is clearly inappropriate. The use of "comprise," "comprises," "comprising" "include," "includes," and "including" are interchangeable and not intended to be limiting. Furthermore, where the description of one or more embodiments uses the term "comprising," those skilled in the art would understand that in some specific instances, the embodiment or embodiments can be alternatively described using language "consisting essentially of" and/or "consisting of."

Definitions

The term "energy storage system" as used herein means some system or means of storing and then accessing energy and may include chemical energy storage systems, such as batteries (rechargeable or not rechargeable), flow batteries or fuel cells; electrical systems such as capacitors or supercapacitors; electromagnetic systems such as superconducting magnetic energy storage systems; or mechanical storage systems such as flywheels or flywheel batteries, springs including micromechanical or nanotech springs such as carbon nanotube springs, or compressed gasses; or thermal storage using thermal batteries, thermocouples, thermopiles or thermionic converters or other means of storing energy.

The term "energy generation system" as used herein means a system which supplies energy to the invention to do work and may refer to solar systems like solar cells or solar batteries; systems which convert kinetic energy into electricity (including electromagnetic induction systems such as a generators, dynamos or alternators that convert kinetic energy into electricity; electrostatic generators; and piezoelectric systems); systems relying on nuclear transformation (such as betavoltaic cells); systems which convert heat into motion or electricity such as turbines or reciprocating engines, either of which may be driven by fuels such as hydrocarbons (including and not limited to natural gas, diesel, gasoline, oil, etc.), gases such as hydrogen or other materials such as chemicals or biomass; and wind systems such as windmills.

The term "air propulsion system" as used herein means a system capable of moving or pressurizing air and may refer to a fan such as axial-flow fans, propeller fans, centrifugal fans (commonly called "squirrel cadges" or "blowers"), mixed flow fans, vane fans, Waddle fans, cross-flow fans, bellows, fans using the Coandă effect, electrostatic fans, turbines, and air compressors including reciprocating, rocking piston, rotary screw, rotary scroll, rotary sliding vane or rotary centrifugal air compressors among others. Air propulsion systems use energy to propel air are thus typically coupled to devices that convert stored or generated energy into mechanical motion including and not limited to motors, turbines or engines or others known to one skilled in the art.

The term "air purification system" or "air supply system" as used herein means a system or component capable of removing contaminants or otherwise undesirable substances from a gaseous medium, in particular air, and may refer to filters (of many different material types and formats such as and not limited to HEPA filters, fabrics, papers, foams, pleats, honeycombs, pellets, cartridges, thick-bed mats, weaves, fibers including artificial and natural fibers such as hemp or coco-fiber, polarized media, ceramic membranes, ceramic mats, packed beds, pellets, beads, granules, carbon materials such as activated carbon, titanium dioxides and others which can use a variety of principles including and not limited to straining, adsorption, interial separation, interception, diffusion, electrostatic attraction, and combined mechanical and electrostatic attraction); sedimentation chambers in which particles can settle out; techniques utilizing particle charge or particle ionization such as in electrostatic precipitators, charged-droplet scrubbing, electric curtains; scrubbers such as plate, packed bed, spray, venturi, cyclone baffle, impingement-entrainment or fluidized-bed scrubbers; wet filtration techniques such as spray chambers or bubbling of air through a liquid such as water; cyclone technology; or high gradient magnetic separation. These air purification systems may be used in combination. These air purification system may also include sterilization technologies including and not limited to photocatalytic oxidation (PCO), especially and not limited to PCO on a titanium dioxide surface with UV irradiation, UV light, biocidal surfaces such as silver or copper coatings or particles or biguanide coatings or compounds (among many others known to one skilled in the art), thermal or pasteurization systems, means of physically sheering pathogens, or radioactive means of sterilization and other methods known to one of ordinary skill in the art.

The air purification system may also, and in preferred embodiments does, include systems or steps capable of catalytic reaction, such catalytic technologies often and not necessarily integrated into filter or filter-like elements, which are familiar and known to one skilled in the art, and which process, break down or remove undesirable substances such as carbon monoxide (CO), ozone ($O_3$), sulfur dioxides ($SO_x$), nitrogen oxides ($NO_x$), hydrogen sulfide ($H_2S$) and similar air-borne sulfur compounds such as mercaptans, organic sulfides, thiophene compounds, thioethers and organic sulfoxides, volatile organic compounds (VOCs) such as hydrocarbons, organic solvents, halogenated organic compounds, benzene and related compounds among many others including those with adverse effects on health and wellness as well as those with noxious odors. Catalysts may including heterogeneous or homogeneous catalysis, organocatalysis, multifunctional solids such as zeolites, alumina, higher-order oxides, graphitic carbon, nanoparticles, nanodots, and facets of bulk materials, transition and late transition elements such as nickel, copper, silver, chromium, manganese, magnesium, vanadium, titanium, palladium, platinum, gold, ruthenium, rhodium, or iridium among many others alone and in combination.

The term "sensors" as used herein may refer to a component that is a type of transducer that detects events or changes in the environment and provide a corresponding output typically as electrical, optical or mechanical signals. Herein, sensor includes and is not limited to accelerometers, gas sensors, acceleration sensors, displacement sensors, motion sensors, proximity sensors, ambient light sensors, cameras and photosensitive or photoreceptive sensors, moisture/humidity sensors, gyroscopes, compasses, microphones, temperature probes of multiple types, chemical sensors, pressure sensors, flow sensors, shock sensors, sensors to detect radiation (by example gaseous ionization detectors like Geiger-Müller tubes, ionization chambers or proportional counters, scintillation counters, semiconductor detectors such as silicon, diamond, germanium or cadmium (zinc) telluride detectors, and similar, dosimeters, or electroscopes among others) and sensors of electromagnetic radiation including and not limited to the UV spectrum and solar radiation, and others including those sensors listed in other sections of this document. The exclusion of one type or class of sensor when sensor is mentioned does not preclude its inclusion in another embodiment of the invention. It is understood that the device records the results of all its sensors constantly and can produce databases, reports or results upon user demand.

The terms "pressure sensors" as used herein may include piezoresistive strain gauges, capacitive pressure sensors using a diaphragm, electromagnetic sensor which measures the displacement of a diaphragm by means of changes in inductance (reluctance), LVDT, Hall Effect, or by eddy current principle, pressure sensors using the piezoelectric effect, optical pressure sensors which use of the physical change of an optical fiber to detect strain due to applied pressure, potentiometric pressure sensors which use the motion of a wiper along a resistive mechanism to detect the strain caused by applied pressure as well as resonant, ionization and thermal pressure detection systems among others known to one skilled in the art. It is noted that pressure sensor classes are often analogous or identical to sensors detecting mechanical motion or stress, and that flow sensors often use those same or similar principles.

The term "pollution sensors" as used herein refers to sensors which detect or measure air quality and may including a wide variety of sensors and technologies selected to suit the particular environment at hand and the insults it may contain. Sensors may be particulate matter detectors, which typically use ionization, photoelectric or optical effects to detect and/or measure particulate. In an ionization detector, a radioisotope produces ionization in air, which is detected, and the concentration of suspended particulates will modulate that ionization. In an optical detector, a light path is exposed to air which contains some concentration of particulate. Depending on the size of particulate and its concentration, it will to some degree be absorbed and scattered, both of which can be detected. It is noted that additional sensitivity can be obtained with long detection paths, or in optical systems, paths in which the light path has been made long through repeated reflection. Gases, volatile organic compounds and biological compounds may be sensed by a wide variety of detectors which may include mass spectrometric detection, carbon nanotubes with antibodies, or antibodies, chemically surface modified micro electro mechanical system (MEMS) sensors, chemo-mechanical sensing with optical detection and capacitive sensing with electronic detection, calorimetric or catalytic bed, catalytic field-effect sensors (MOSFET), conducting polymer, electrochemical, metal oxides semiconducting (MOS), optical sensors, quartz crystal microbalance, selective sensors with sensitive layers based on polymer- or heteropolysiloxane for $CO_2$, tin dioxide CO detectors, $SnO_2$—Ag on ceramic wafer $H_2S$ sensors, yttria-stabilized zirconia (YSZ) oxygen sensors, $NO_x$ and $SO_x$ detectors, optic ozone detectors, gas analyzers, nondispersive infrared sensor, infrared point sensors, electronic nose and surface acoustic wave sensors among others and other methods known to one of ordinary skill in the art.

The term "airflow monitor" or "airflow sensor" as used herein means some component or system capable of detecting and/or measuring the flow of gases such as air and may refer to vortex-principle airflow sensors, solid-state airflow sensor or optomechanical sensors (often with micro cantilevers), rotameters, spring and piston flow, ultrasonic flowmeters, turbine flowmeters, paddlewheel sensors, anemometers or hot wire anemometers among other methods known to one of ordinary skill in the art.

System for Shielding from Air Contamination

One aspect of the present application is a system for shielding the face of a user from contamination present in air. FIG. 1 shows one preferred embodiment of the system for shielding from air contamination. A housing (101) contains an air propulsion system (102) and air purification system (103) to remove contaminants from the air with an air intake (104) drawing in air that may contain contaminants. The housing may also contain in whole or in part interconnected energy storage systems, energy generation systems, and air propulsion systems, as well as control circuitry. In some embodiments, energy generation systems and/or energy storage systems, which typically represent a significant portion of the invention's weight, may be separate from the housing. The housing is designed to be suitable for transport and use; in preferred embodiments, it is lightweight and convenient to put on and take off. In one embodiment, this housing may be attached to and removed from the garments of a user. Due to the desire to balance considerations of the weight of the housing against its portability, embodiments designed for extreme lightweight and portability may be reduced in clean-air generation ability. In another embodiment, this housing is secured to a convenient place, such as the hip or belt of a user (see FIG. 14), by some convenient means such as a clip, strap, string, Velcro or other method, such as over the shoulder as a shoulder bag, under, on or around the arm or wrist, as a backpack or supported from the neck, shoulders or head. It may also be carried or placed in a location next to the user, such as on a table while sitting or on a seat while driving. The housing is designed to be portable and functional as the user moves, affording protection during the user's activities. A person of skill in the art will understand that the particular choice and design of any housing and means of carrying the device is not limiting on the invention.

In a preferred embodiment, all moving air may pass first through the air purification system before reaching an air propulsion system; in such cases the air propulsion system draws in external air and emits cleaned air. A person of skill in the art will understand that the particular choice and design of any energy storage systems, energy generation systems, or air propulsion systems is not limiting on the invention. Likewise a person skilled in the art will recognize the air purification system may be placed after, rather than before, the air propulsion system and that such an arrangement may require regular cleaning of the air propulsion system and is thus less desirable.

The air intake may connect to a filter (103) functioning as the air purification system. In preferred embodiments, consumable elements of the air purification system (such as but not limited to filters) are easily accessible and replaceable, for example by being formed in easy-to-exchange, cartridge-like units which may be disposable and/or recyclable. In certain embodiments, an air purification system may not be within the housing, in which case the air purification system will be located between the airflow exiting the housing, likely within the a flexible air delivery system, and before air manifold system. A person of skill in the art will understand that the particular choice and design of any filter, as well as the placement of the air purification system before or after the air propulsion system, is not limiting on the invention.

Figure 11:
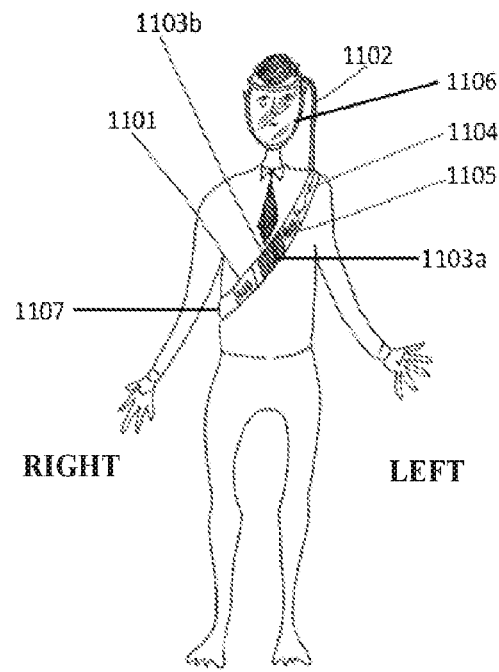
FIG. 11 shows the invention in a preferred sash embodiment from the front in which all systems (energy storage, air propulsion, air purification, air supply and control systems) are built within the sash.

The air propulsion and air purification systems have controls (105a) and indicators (105b) interfacing with control circuitry (see also FIG. 11, 1101). Controls and control circuitry consist minimally of a means to control the air propulsion system and are, for example in electrically driven systems, at minimum a simple on/off switch. Controls and control circuitry may also control the volume and pressure of delivered air for example through modulation of the speed or power of the air propulsion system as a function of external condition (like wind), air purification system condition (such as a dirtied filter) or user condition (such as inhalation or preference for air flow) among other factors. The exact nature of the controls and control circuitry will depend on the nature of the drive system for the air-propulsion system. In various embodiments, the controls and control circuitry ranges in complexity from a simple switch to a computer with significant processing power. Controls will be different in wholly mechanical systems. For example, where rotary power is derived from a flywheel to directly drive the means to propel air, in such cases, all or mostly all mechanical means such as transmissions or variable transmissions may be employed.

An air exit (106) leads to an air delivery system (107), this air delivery system being flexible in preferred embodiments. The air propulsion system(s) contained within the housing is designed to expel air into and through the air exit into the (preferably flexible) air delivery system. Cleaned air can be carried through the air delivery system by tubing, hosing, cowling, baffling, channels, piping or otherwise enclosed space capable of transferring the cleaned air to the manifold system while preventing mixing with uncleaned air. The air delivery system is preferably made of lightweight material(s), is, as needed, flexible, flexibility imparted by example through the use of flexible materials or moveable segmentations, and is designed to minimize the loss of gas pressure from the air supply to manifold system. As lightweight materials may have collapsible thin walls, the air supply may have additional support structures such as plastic or metal coils to support it. A person of skill in the art will understand that the particular choice and design of any material used for the air delivery systems is not limiting on the invention. In preferred embodiments, the air delivery system may be hidden within an aesthetically pleasing design, such as the shoulder straps of a side-bag or backpack, or within or under clothing.

The flexible air delivery system supplies cleaned air from the air purification system to a manifold system (108). The manifold system provides gas to each air supply system; optionally the manifold system can passively or actively modulate the relative amounts of gas transferred to each system for example in response to environmental conditions or user preference. As with the air delivery system, the manifold system is preferably designed to be lightweight and minimize any pressure losses without interfering with the function of the support system. The manifold system consists of tubing, hosing, cowling, baffling, channels, piping or otherwise enclosed space capable of transferring the cleaned air supplied through the flexible air delivery system without mixing with ambient air. In one embodiment, the protection pane itself is part of the manifold system, air being provided between two juxtaposed protection panes, the innermost pane of which has holes, apertures, screens, ports or otherwise means to direct the air to the first and second air supplies.

The manifold system may be, and in preferred embodiments is, built into a support system (109), for example the manifold system may be formed wholly or partially by hollow head supports which position the protection pane in front of the face. As a manifold, the manifold system separates the clean air from the flexible air delivery system into at least two down-stream airflows: firstly to the space between the user's face and a protection pane (this represents the majority of air for breathing and displacing polluted air), and 2) to the delivery system integrated with the protection pane (110). The support system for the manifold system and protection pane on or around the head may typically include bands, clips, straps, hats, headsets, helmets, or shoulder supports and in preferred embodiments supports the worn device directly on the head with securing bands, straps or arms going at least partially around the head.

While it may conveniently double as part of the manifold system, the main function of the support system is to hold the protection pane in front of the user's face. This pane may be fixed to the support means (i.e. it cannot be flipped up) or it may be jointed so that it can be lifted up. The protection pane affords protection from projectiles, particles or fluids which would otherwise contact the user, and must be clear enough for the user to see through. The protection pane may be made of any material suitable to such ends including and not limited to plastics which one can see through, hardened glass, leaded glass, mica, transparent composites or other similar transparent or semi-transparent materials. In the preferred embodiment, the protection pane is curved to roughly encircle and/or match the shape of a user's face (see also FIG. 10).

Figure 13:
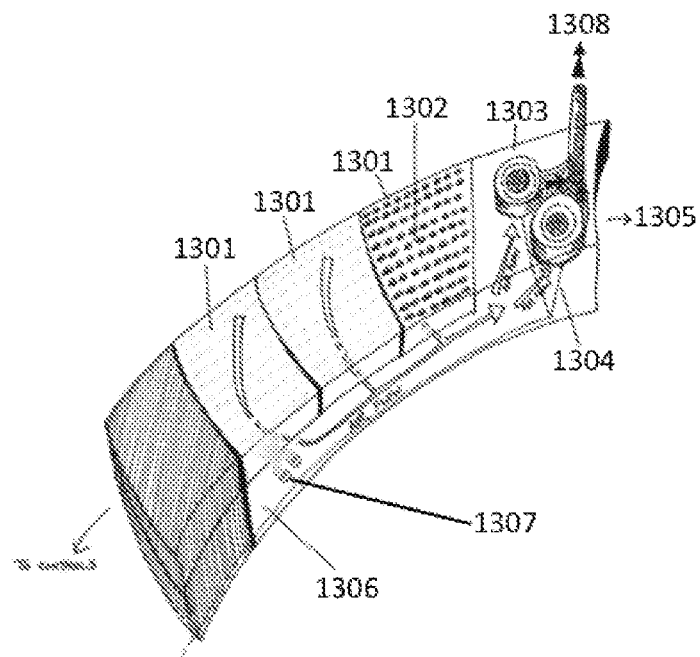
FIG. 13 shows a diagrammatic view of the sash embodiment of the invention and how air flows.
Figure 14:
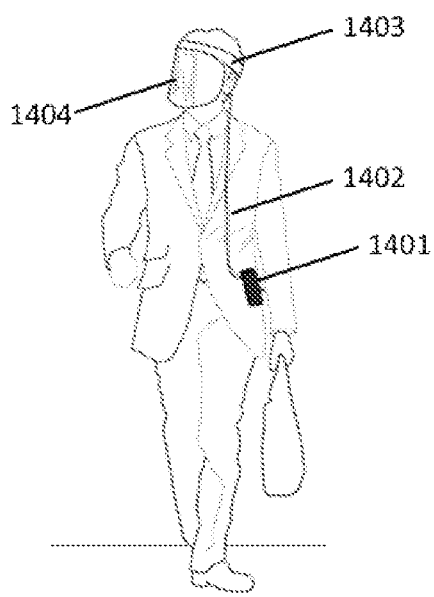
FIG. 14 shows how the invention is modular with separated air supply systems worn on the body and protection pane with air delivery worn on the head.
Figure 15:
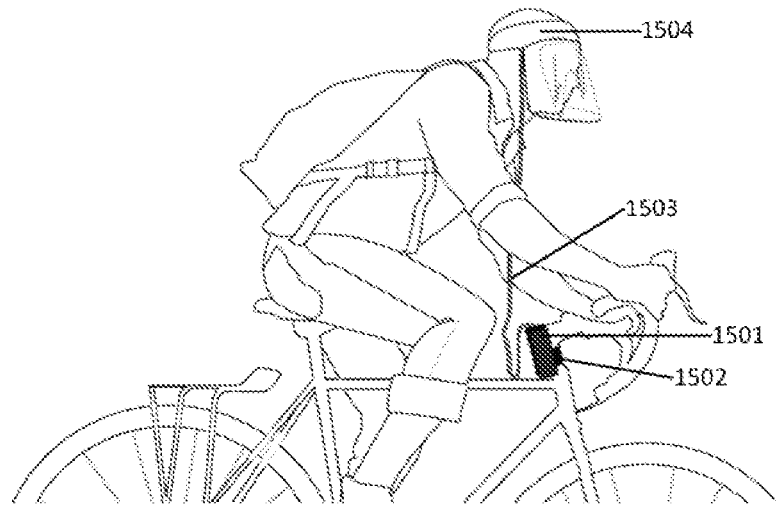
FIG. 15 shows how the invention may be supported by a vehicle, in this case a bicycle, for maximum comfort.
Figure 16:
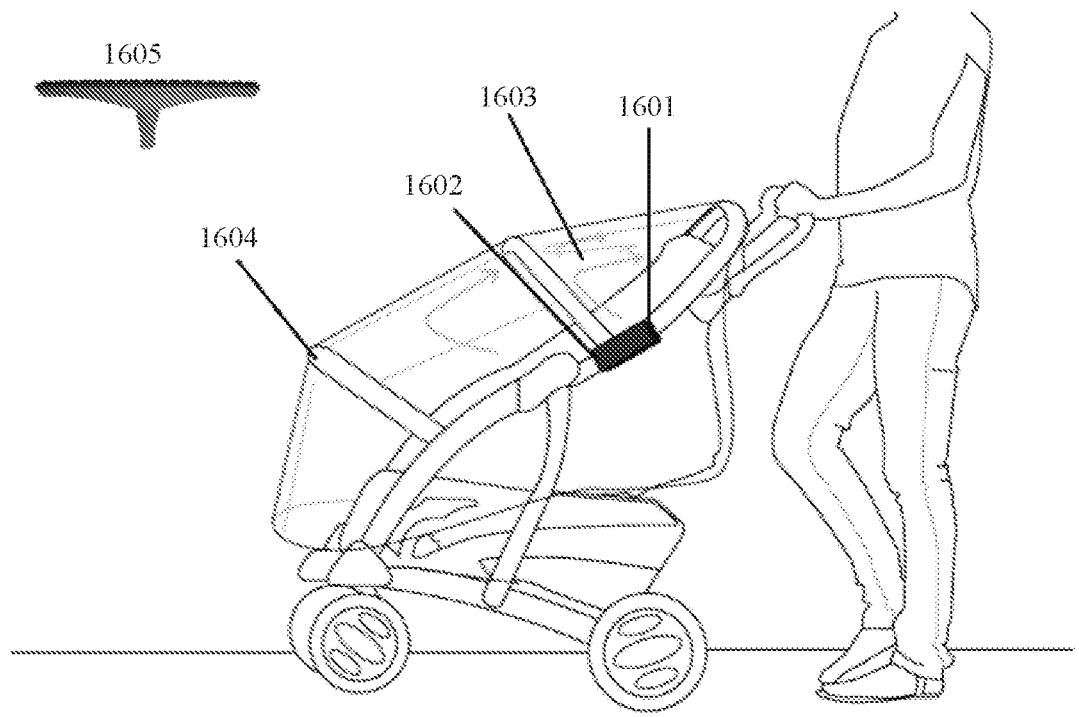
FIG. 16 shows how the invention may be supported by a vehicle, in this case a stroller, and thus provide air to the interior of a sealed space.

In a preferred embodiment, all systems are able to be integrated into one unit worn by the user on their body or carried in a bag or in or on a vehicle or means of transport such as a car, bicycle or stroller (see FIGS. 14, 15 and 16). It is contemplated the device may also have attachments to allow the air supply system to provide air to an enclosed space in which the protection pane is not needed, such as a car or stroller (see FIGS. 15 and 16). In a particular embodiment, the flexible air delivery system may be attached to or contained within the sash, belt or support strap of a satchel, side-bag, fanny pack or similar so that, for example, the housing may be contained within the satchel while air is conveniently delivered to the head of the user, and the belt of the satchel is over the shoulder of the user when the user is walking or bicycling (see FIGS. 11, 12, 13, 14 and 15). Alternatively, the housing and air purification system can be belt mounted or secured to the user's belt (see FIG. 14). All systems may also be contained in a backpack configuration, with or without space for storage of other items. In another preferred embodiment, the housing, air purification system and a section of the preferably flexible air delivery system are fully integrated into a sash worn by the user and made flexible through the use of segments (see FIGS. 11, 12 and 13).

In other embodiments, the systems are separated into multiple components (for example an air supply box containing the housing and air purification system, an air supply system tube and separate head-worn air delivery systems; see FIG. 14). It is further noted that energy storage or generation systems can have significant weight, and that weight typically increases as the capacity of energy. This fact leads to advantages of separating the unit, especially the means of energy storage/generation and means to move air, for longer unit life. Similarly it may be advantageous to offer a light (and thus shorter-lived) device in which all component systems are integrated and mounted in one unit typically worn on the head.

Figure 2:
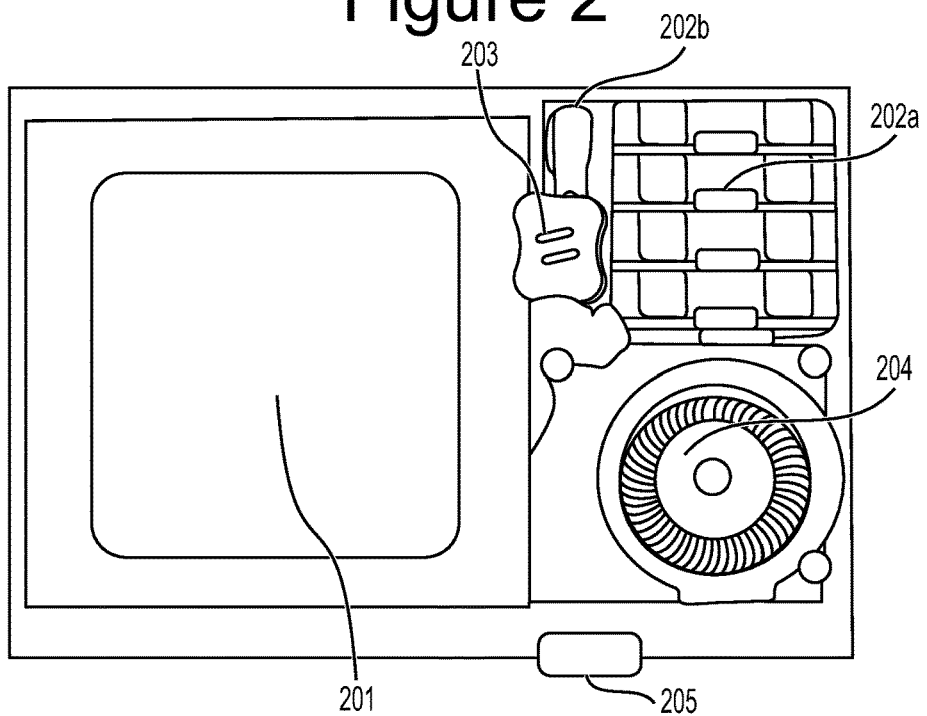
FIG. 2 shows the interior of the air filtration system component of the facial shielding system.

FIG. 2 shows an internal view of an embodiment of the housing. (See also FIGS. 7, 8 and 9 The housing is shown containing a filter (201) to remove contaminants from the air; an energy storage system (202a); an interface to recharge the energy storage system (202b); control circuitry (203); an air propulsion system (204); and an air exit (205). Not shown in this embodiment of the housing containing the air supply system and an embodiment specifically contemplated by this patent is a means to monitor the quality of air being delivered in particular air pollution sensors and their corresponding circuitry. A person of skill in the art will understand that the particular arrangement and design of components within the housing is not limiting on the invention.

In certain embodiments, check valves which allow flow in only one direction are added at various points in the paths of airflow to prevent wind or other ambient air currents from push pollution into the air purification system. Such valves may include ball check, diaphragm, swing check or tilting disc check, stop-check and lift-check, as well as in-line check valves, any of which may be chosen to optimize performance at the air pressures present in this invention (typically low pressures).

In other embodiments, interfaces to connect to the power systems of other electronic devices or power sources may be added for the supply or recharging of stored energy, especially electrical charge in, for example, a battery or capacitor, and physical momentum in a flywheel battery (see FIG. 2, 202b). Specifically contemplated, in the case of the air purification system being powered by batteries, is an interface to electricity provided through USB ports, interfaces to the electrical systems of cars and to standard wall outlets of homes and offices. Such interfaces are typically standard involving connectors, voltage conversion and regulation as necessary, current regulation other systems and methods known to one of ordinary skill in the art. It is noted that compressed gas can be used as a means of energy storage and/or the source of purified air or other gases and that energy and/or gases to be supplied can be recharged by simply by connecting to a compressed gas source of higher pressure. Finally, it is contemplated that the device may be recharged and/or powered wirelessly though wireless power transfer techniques (WPT) including non-radiative techniques such as near-field inductive (magnetic) coupling including resonant inductive coupling or capacitive coupling including resonant capacitive coupling or through electrical conduction such as atmospheric plasma channel coupling or by magnetodynamic coupling or though far-field radiative techniques like microwaves or lasers or alternatively by energy harvesting technologies. The implementation of these technologies is clear to one skilled in the art.

Figure 3:
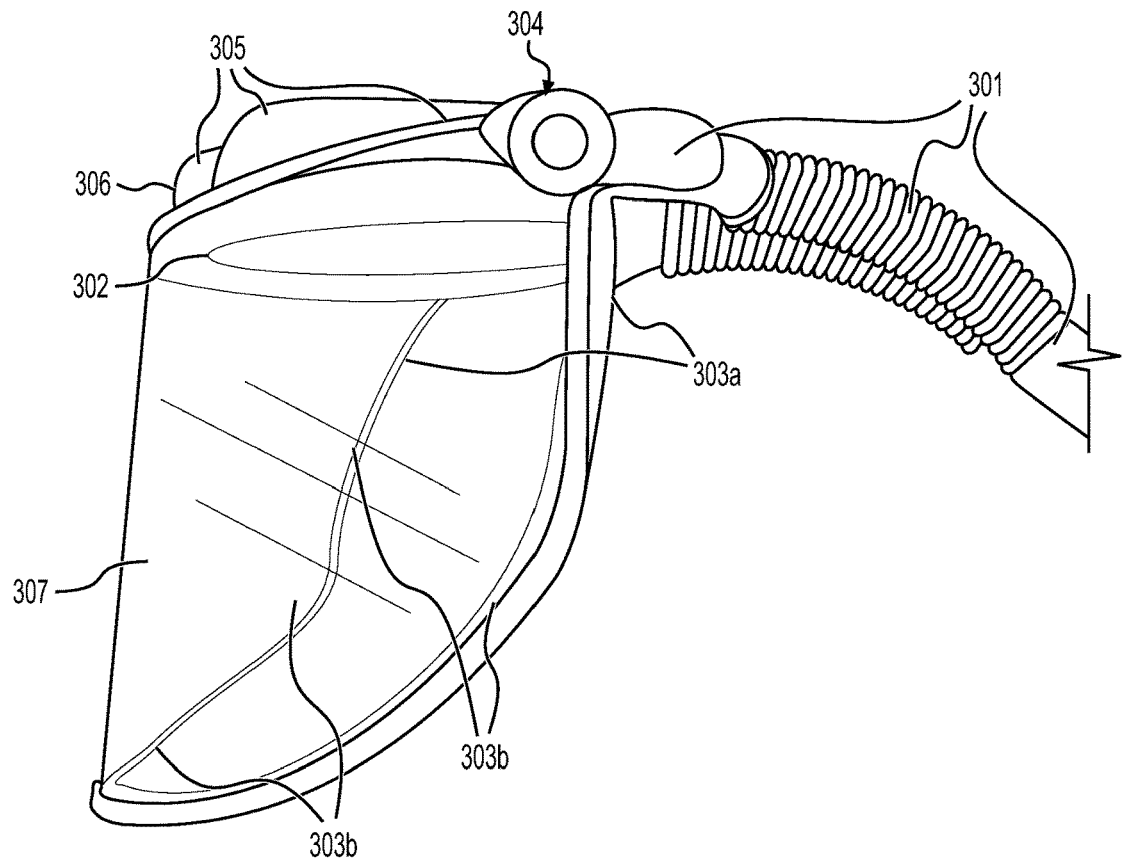
FIG. 3 shows the head mounted device component of the facial shielding system.

FIG. 3 shows a side-view of the head mounted device component of the shielding system. The head mounted device is connected to part of the manifold system (301) which supplies clean air into a first air supply system (302) with apertures and a second air supply system (303a) with apertures (303b). The device has an optional hinge (304) where the protective pane joins the support system (305), which can enable a user to raise the protection pane without removing the head mounted device from the head of the user. There is a seal (306) between the support system and the protective pane. Protection panes are in the preferred embodiment detachable, interchangeable and adaptable to different designs, strength of impact, or desirable airflow patterns. In certain embodiments, for additional protection and sealing, a skirt of fabric, plastic, leather, ultrafine screen or similar appropriate materials which can further isolate the airflow and face of the user and that rests on or attaches to the user's upper body or some portion of the upper body or clothing worn on the body, is added to the head mounted device, this skirt being optionally removable and re/detachable. In the case of environments which contain or possibly contain dangerous hazards (such as airborne biological pathogens or toxic airborne chemicals), this skirt may be drawn tight against the skin, fully enclosing the space, or alternatively may attach to specially made clothing (such as a jacket or coat) with specially designed seals (see FIG. 17, 1701).

Figure 4:
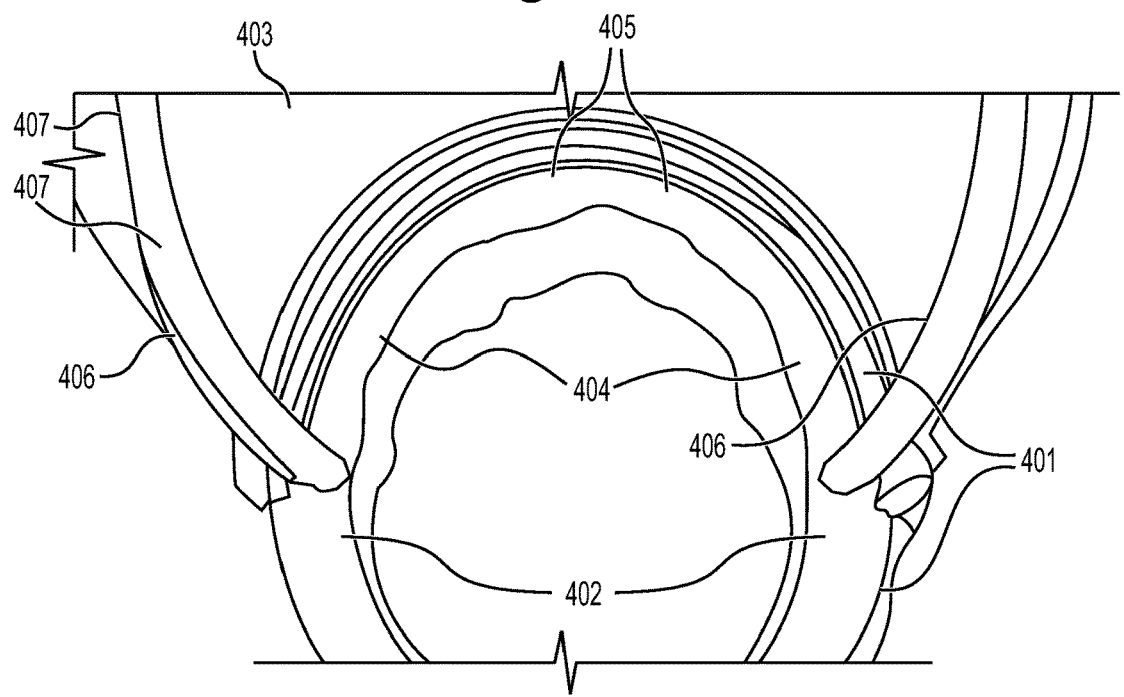
FIG. 4 shows the first and second air supply systems that are contained within the head mounted device component from the point of view of the underside of the head mounted device component.

FIG. 4 shows an underside view of the head mounted device. The support system (401) is attached to the manifold system (402) which carries air around the top of the protection pane (403). The first air supply system (404) and its apertures (405) take cleaned air from the manifold system and supply it to the space between the user's face and the protection pane. This clean air displaces contaminant-containing air, thereby supplying clean air to the user to breathe. The majority of air cleaned by the air purification system goes to the first air supply system. The second air supply system (406) and its apertures (407) take cleaned air from the manifold system and delivers airflow roughly perpendicularly to the plane of the user's face (see also FIGS. 7, 8, 9 and 10). This creates gaseous flows in an enclosing direction that encircle and enclose the airflow of the first air supply system, in particular and especially around the sides of the face, thus reducing and preventing mixing with external air (see also FIG. 10). A person of skill in the art will understand that the direction and flow-rate of gas flowing from the apertures of the second air supply system may be varied if need be. This patent contemplates that both the first and the second air supply systems may be made user-adjustable in both flow and direction.

Figure 5:
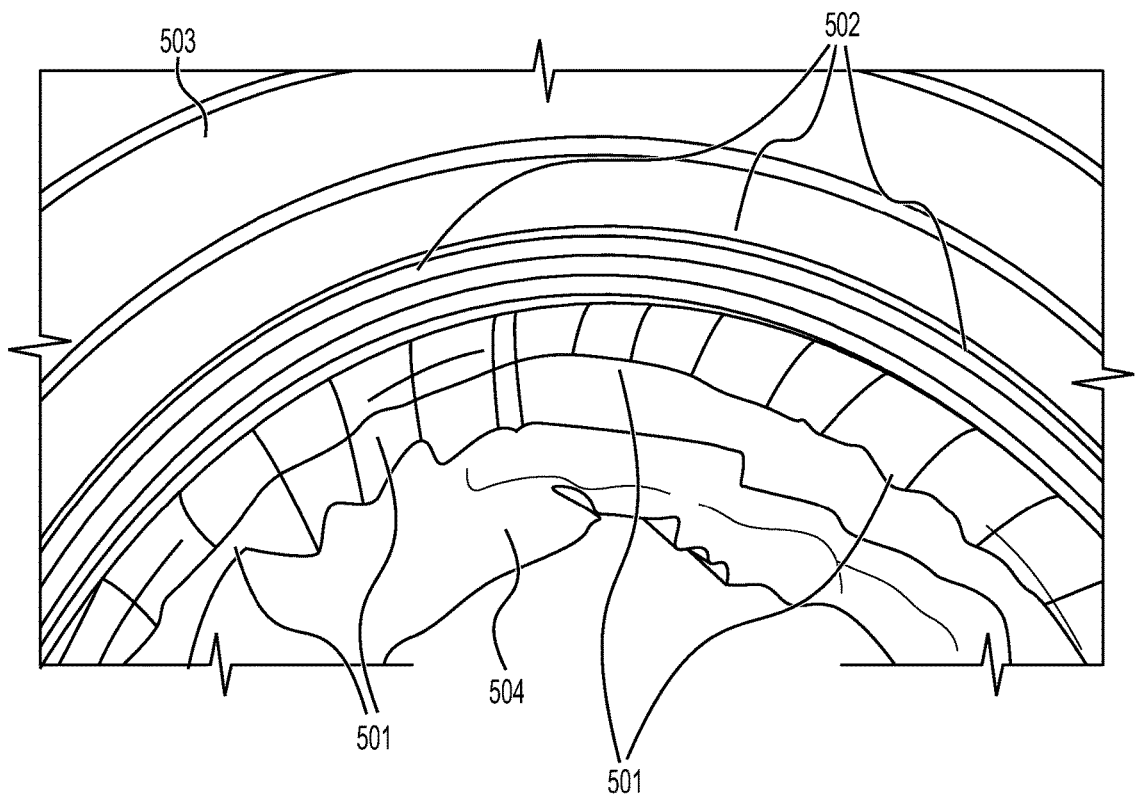
FIG. 5 shows a detail of the first air supply system.

FIG. 5 shows a detail of the apertures of the first air supply system (501) in relation to the support system (502) and the protection pane (503). The air flowing through the apertures of the first air supply system is preferably directed either from top to bottom (i.e. from roughly the position of the support system) or from bottom to top (i.e. from the bottom of the protection pane to the support system; this would be most applicable in systems further sealed with the addition of a skirt; see additionally FIGS. 7-10 and 17). Because a degree of air sealing is afforded by the support system mounting typically on or against a user's head or forehead, especially when the support system is afforded a soft sealing mechanism such as foam which conforms to the user's body (504), is most preferably from top to bottom. Other airflow patterns are also possible. For example, two or more airflows which are opposed to each other can be supplied from opposite sides of the protection pane (from the left and right) and meet in the center of the face. Bound by the protection pane, the airflows collide, thus supplying clean air which flows towards the mouth/nose. Alternatively, air can be directed to flow across the face. In a preferred embodiment, where air is supplied from around the top of the user's head, airflow in the region around eyes can be reduced, thus reducing eye drying. The apertures through which the airflow is directed can consist of holes, slits, screens, etc., as well as baffles as needed to direct the flow of air (see FIG. 7). In the preferred embodiment where air is supplied from the top, airflow around eyes can be reduced by narrowing the apertures, such as through a slit which is narrower directly above the eyes. The air supply system may also be formed fully or partially within the protection pane. For example, by having an exterior protection pane and an interior protection pane, and with holes in the interior protection pane strategically located in the region of the user's mouth and nose, the protection pane itself can supply clean air (see FIG. 17, 1702). Alternatively, tubes may be mounted on the protection pane supplying air from the manifold system directly to the user's mouth and nose (see FIG. 17, 1703). In all embodiments, the air supply systems are designed to minimally hamper vision by being made of transparent materials, by being as small in size as is possible for a given performance level and by their placement to minimally hamper vision.

Figure 6:
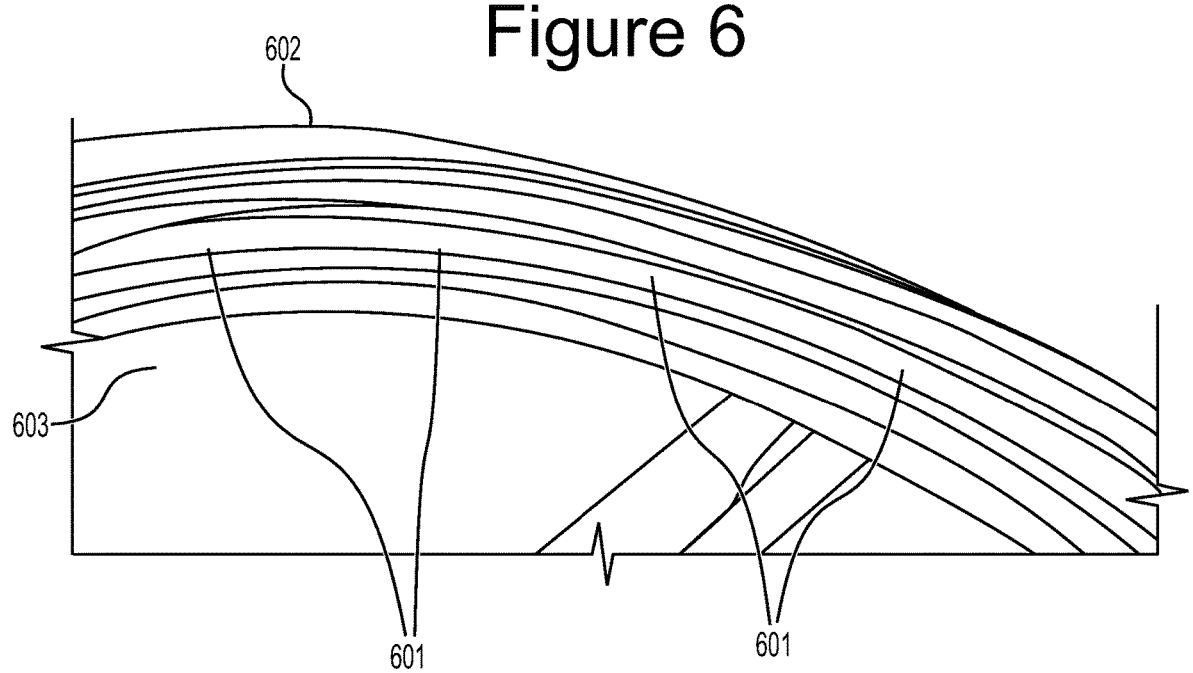
FIG. 6 shows a detail of the second air supply system.

FIG. 6 shows a detail of the apertures of the second air supply system (601) in relation to the edge of the protection pane (602) and the protection pane (603). The air flow through the apertures of the second air supply system, directed roughly perpendicular to the user's face, obviates the need for either high gas flow through the first air supply system, which would be necessary in the absence of sealing against the user's body (to displace contaminated air by sheer volume of mass flow), or the absence of sealing skirts which would otherwise rest on the upper body of the user. By sealing without physically touching the user's body, this second air supply system thus provides for comfort and simultaneously provides for less airflow and decreased energy usage (compared to an unsealed design that relied on a single air supply system). In addition, sealing without touching the user's body allows for adequate protection for users with jewelry, facial hair, glasses and other conditions that would prevent the use or efficacy of standard respiratory masks, in addition to being more comfortable. As with the first air supply system, the apertures through which the airflow is directed can consist of holes, slits, screens, etc., as well as baffles as needed to direct the flow of air (see also FIG. 7). Also, as with the first air supply system, the second air supply system may be built into the protection pane itself. In one such embodiment in which air is supplied between two panes, the second air supply system can be comprised of apertures in the inner pane that roughly encircle the periphery of the protection pane, such apertures being for example slits. In the case of a hinged protection pane, the second air supply system is preferably afforded with valves that shut off airflow to the second air supply system when the protection pane is lifted up. For example, tubes from the manifold system may pinch closed when the protection pane is raised. In preferred embodiments, flow control is adjustable to allow for different face shapes and preferences of where flow from the second air supply system contacts the user's face. Such control can be afforded with mechanical means (valves) or electromechanic means (solenoids or piezoelectric actuators for example) and other methods known to one of ordinary skill in the art. Under test conditions, with contaminated air measured at 450 μg PM2.5/m$^3$, a preliminary working prototype system assembled as shown in FIGS. 1-6, but with non-optimized air supply systems, produced an over 80% reduction in air contamination levels.

Figure 7:
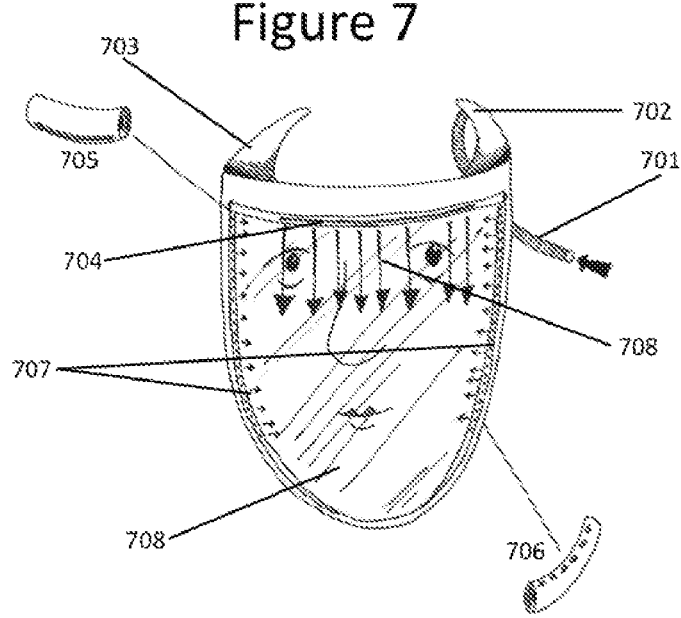
FIG. 7 shows aspects of the head mounted device and the airflow patterns of the preferred embodiment.

FIG. 7 shows aspects of the head mounted device and the airflow patterns of the preferred embodiment. Air from the air purification system (not shown) enters from the flexible air delivery system (701) into the manifold distributing air to the first and second air supply systems (702), the head mounted device component being held on the head by the support system (703). The first air supply system (704) typically delivers the bulk of the air to breathe, here from the top of the head mounted component of the device (airflow shown by 708). Apertures may be of various forms such as slits (705) or alternatively holes (706) or other form which allows cleaned air to exit and be directed. The second air supply system (707) supplies an airflow to enclose and partially or mostly encircle the face and air flow of the first air supply system in particular on the sides.

Figure 8:
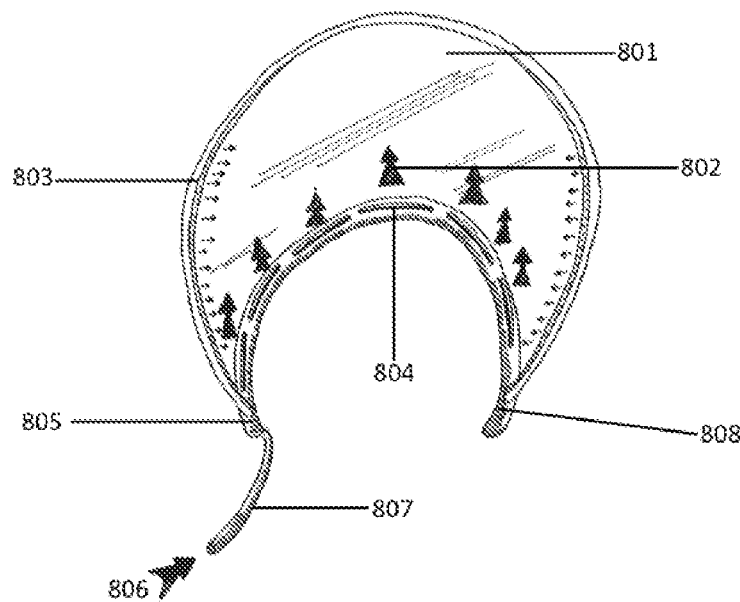
FIG. 8 shows the first and second air supply systems that are contained within the head mounted device component in relation to the protection from the point of view of the underside of the head mounted device component.

FIG. 8 shows the first and second air supply systems that are contained within the head mounted device component in relation to the protection from the point of view of the underside of the head mounted device component. Air entering from the air supply system (806) delivered via the flexible air supply system (807) to the air manifold (805) for distribution to the first air supply system (804) and second air supply system (803), whereby the second air supply system is directed roughly parallel to the face and partially or mostly encircles the face and especially airflow of the first air system. Air from the first air supply system typically is the majority of air flow from the air purification system (802) and is prevented from mixing on the sides by the second air supply system (803) and on the front by the protection pane (801). The head mounted device is held on the head by the support system (808).

Figure 9:
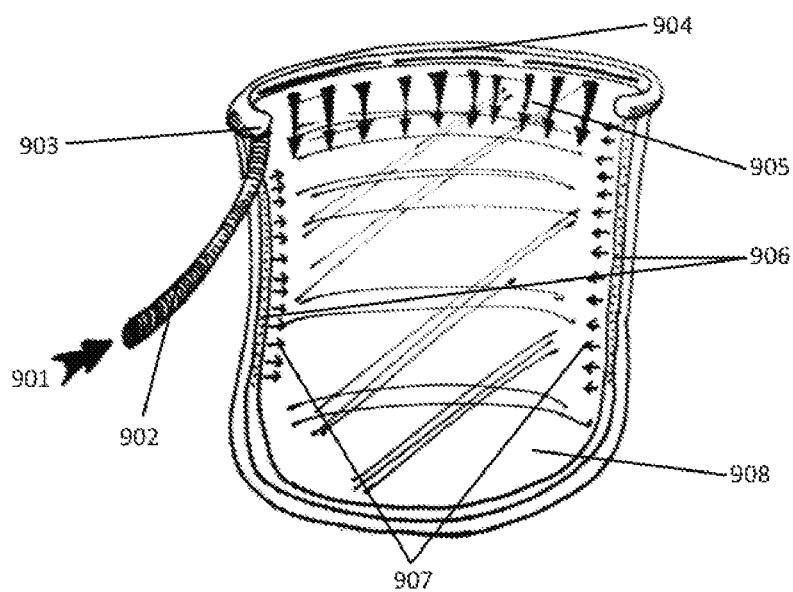
FIG. 9 shows the head mounted device component from the inside (perspective of the user) showing the airflow patterns of the first and second air supply systems.

FIG. 9 shows the head mounted device component from the inside (perspective of the user) showing the airflow patterns of the first and second air supply systems. Air supplied by the air purification system (901) delivered via the flexible air supply system (902) to the air manifold (903) for distribution to the first air supply system (904) through its apertures and second air supply system (906) through its apertures, whereby the second air supply system is directed roughly parallel to the face and partially or mostly encircles the face and especially airflow of the first air system. Air from the first air supply system typically is the majority of airflow from the air purification system (904) and is prevented from mixing on the sides by the second air supply system (907) and on the front by the protection pane (808).

Figure 10:
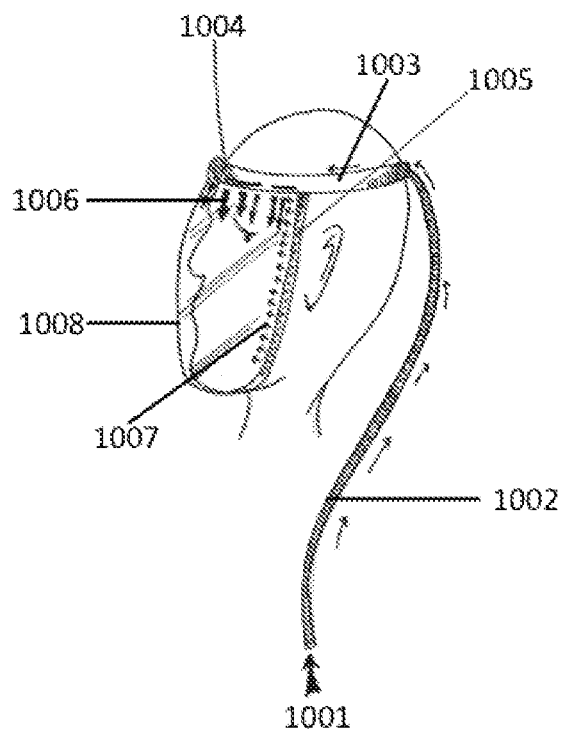
FIG. 10 shows the head mounted device component and the airflows of a preferred embodiment of the first and second air supply systems and how the second air supply system roughly encircles the face of the user

FIG. 10 shows the head mounted device component and the airflows of a preferred embodiment of the first and second air supply systems and how the second air supply system roughly encircles the face of the user. Air supplied by the air purification or air delivery system (1001) delivered via the flexible air supply system (1002) to the air manifold fully integrated into the support system (1003) for distribution to the first air supply system (1004) through its apertures and second air supply system (1005) through its apertures, whereby the second air supply system is directed roughly parallel to the face and partially or mostly encircles the face and especially airflow of the first air system (1007). Air from the first air supply system typically is the majority of airflow from the air purification system (1006) and is prevented from mixing on the sides by the second air supply system (1007) and on the front by the protection pane (1008). Note the curvature of the protection pane (1008) for additional comfort and protection of the user.

FIG. 11 shows the invention in a preferred sash embodiment from the front in which all systems (energy storage, air propulsion, air purification, air supply and control systems) are built within the wearable, quick-to-don sash. Controls and indicators (1101) are easily viewed, accessed and operated on the front of the sash by the user. In one sash embodiment, air purification is provided for by multiple filters (1103a), segmented to allow flexibility (1103b) with airtight seals between with an air propulsion system (1105) powered by batteries or another energy storage system balancing the front and back weight sash on the back of the user (see FIG. 12). Power is supplied to the controls via a flexible power supply cable (1104) The flexible air delivery system (1102) is routed through the sash; within the sash the flexible air delivery system typically takes the shape of a roughly rounded rectangle, not round, to match the geometry of a sash (like the flat straps of a backpack). Clean air is then routed out of the sash to provide clean breathable air to the head mounted portion of the device (1106) where the first and second air flow systems described above protect against contaminated air and where the protection pane provides protection against electromagnetic radiation (especially UV) and also protects from projectiles. The sash may be afforded with a release/and or connecting mechanism (1107) to provide for ease of donning and release if the sash is caught. Such mechanisms include breakaway systems well known to one skilled in the art and might include magnets, friction fittings, sheerable or breakable components with a known breaking strength or similar or alternatively simple clasps or buckles or similar.

Figure 12:
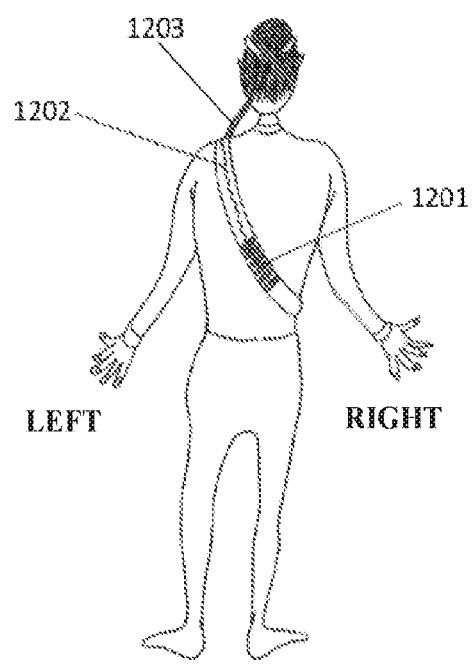
FIG. 12 shows the invention in a preferred sash embodiment from the back in which all systems are built within the sash.

FIG. 12 shows the invention in a preferred sash embodiment from the back in which all systems are built within the sash. The energy storage system (1201), here rechargeable batteries, which typically represents a large portion of the total weight of the full invention, is segmented to maintain flexibility of the sash and located on the opposite side of the other components (the back). Power is provided to the control circuitry and air propulsion system via a flexible wire. Its vertical position is balanced such that the sash embodiment will not rotate while the user moves about. This embodiment is one of the most preferred embodiments as it is close to the body protrudes minimally, reducing the chances of catching. In the preferred embodiment components of the invention in this form are removable for easy washing of the sash.

FIG. 13 shows a diagrammatic view of the sash embodiment of the invention and how air flows. Air purification means, in this case segmented filters (1301) with airtight seals between them covered by a porous cover (1302, shown only once) have air drawn through them by thin blowers (1303) controlled by the controller (down and to left as drawn) with power supplied by batteries on the back (1305, compare FIG. 12). The design is such that the unit is flexible and the thickness of the blowers and filters allows air to flow in an airspace below (1306) to be routed to the head mounted portion of the device (1308). In this preferred embodiment, UV LEDs (1307) are illuminating a titanium dioxide back of the filters (not visible, under all filters 1301; only two LEDs shown) for photocatalytic oxidation (PCO) of volatile organic compounds (VOCs).

FIG. 14 shows how the invention is modular with separated air supply systems worn on the body and protection pane with air delivery worn on the head. The air purification unit is attached to a belt or clothing or similar (1401), thus relieving the head of the majority of weight from the energy storage system and air purification system. Clean breathing air is supplied via the flexible air delivery system (1402) to the head mounted device through the manifold (1403) integrated into the support system. The user is protected by the protection pane (1404).

FIG. 15 shows how the invention may be supported by a vehicle, in this case a bicycle, for maximum comfort. The air purification system (1501) is supported by a means of attachment (1502) to a vehicle, in this case a bicycle. Such a means of attachment is contemplated above and may be a clip, snap, Velcro or similar. Clean breathing air is supplied via the flexible air delivery system (1503) to the head mounted component of the device (1504)

FIG. 16 shows how the invention may be supported by a vehicle, in this case a stroller, and thus provide air to the interior of a sealed space. The air purification unit (1601) is attached to an enclosed space, here a vehicle and specifically a stroller (1604) by means such as be a clip, snap, Velcro or similar (1602). The clean air is then routed into the enclosed space by the flexible air delivery system to allow for circulation (1603). Air so provided by the flexible air delivery system may be distributed and made more comfortable by air distribution system attachments (1605) which distribute the cleaned air within the enclosed space.

Figure 17:
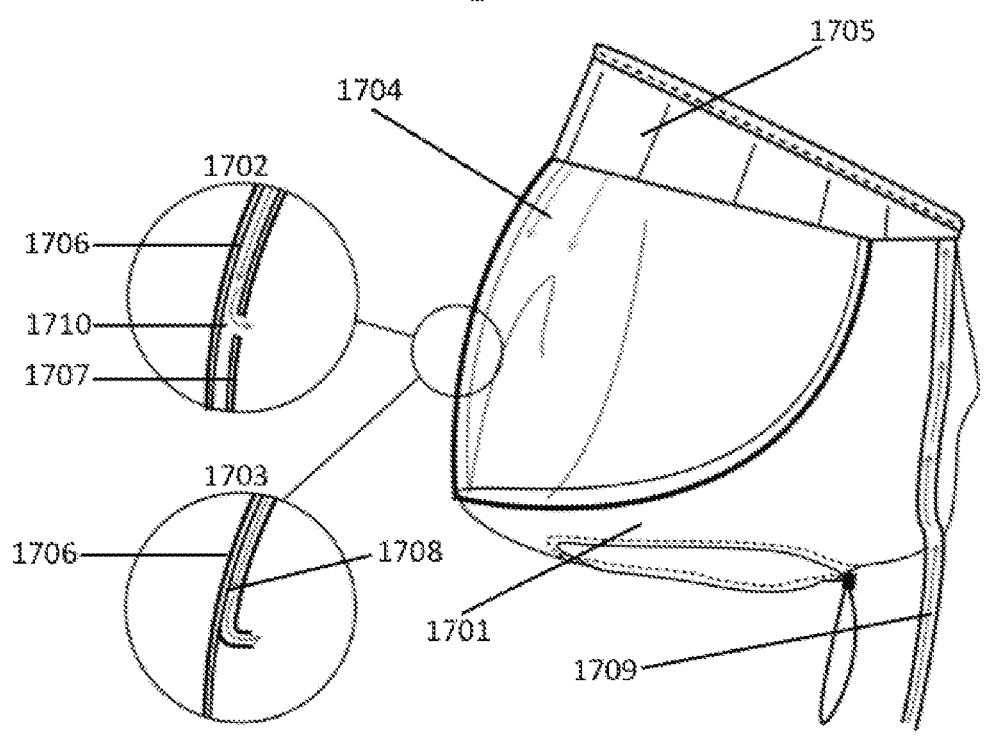
FIG. 17 shows the head worn protection pane and air delivery system with a closeable skirt for use in extremely high pollution environments, and how the protection pane itself may form part of the second and/or first air supply systems.

FIG. 17 shows the head worn protection pane and air delivery system with a closeable skirt for use in extremely high pollution environments, and how the protection pane itself may form part of the second and/or first air supply systems. Air delivered via the flexible air delivery system (1709) to the manifold detailed in other figures and integrated into the support system (1705) is delivered in addition to the embodiments of the first and second air supply systems shown above by two means. First, air is delivered between two panes, an outer pane (1706) and inner pane (1707). Holes (1710) between these two spaces allow air to be provided directly to the nose and mouth of a user (insert 1702). Second, tubes (1708) along the protection pane can supply air directly to the nose and mouth (insert 1703). In areas of high pollution, to fully prevent contaminated air from reaching the user, a skirt of appropriate material (1701) can be pulled tight or may have elastic. This skirt may be on the sides, bottom, or fully around the head of the user.

Figure 18:
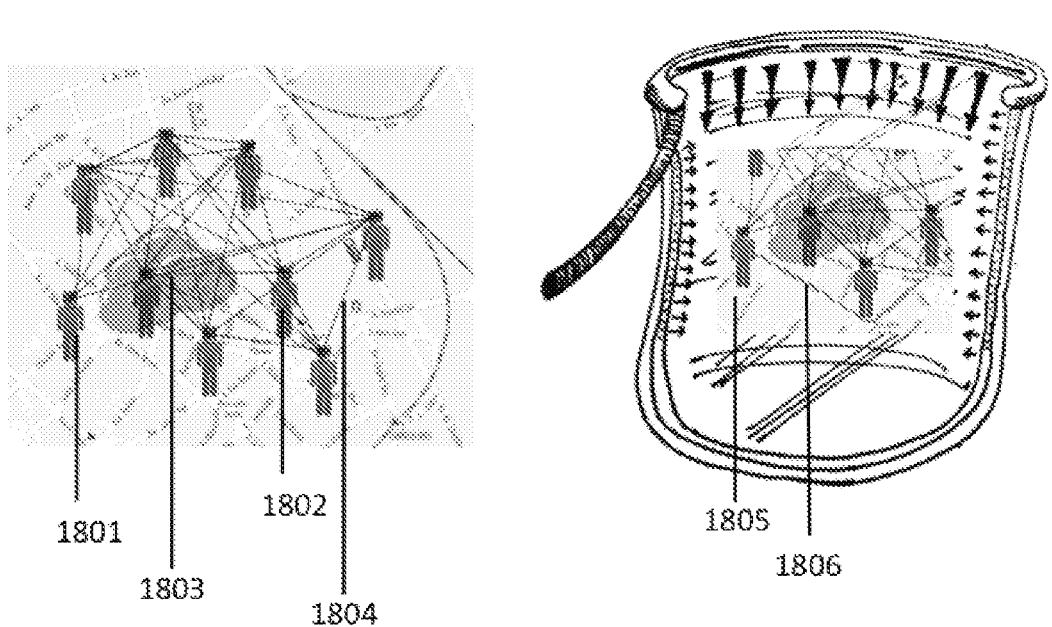
FIG. 18 shows devices in communication with each other as to pollution status and other data measured from their sensors.

FIG. 18 shows devices in communication with each other as to pollution status and other data measured from their sensors. Person 1 (1801) desires to travel to person 2 (1802). However, pollution stands between them (1803) and is measured by devices in that vicinity. The devices worn are in constant communication between themselves, either directly (as shown, 1804) or indirectly through the internet or other communication systems. Each device is thus aware, in real time, of where pollution, traffic, heat and other parameters are. Person 1 indicates to the device that they wish to travel to person 2 (either verbally or through other data entry means) and the device calculates and displays on a heads up display on the interior of the protection pane (1805) the best path to travel to avoid pollution and other undesirable effects (1806). The same technique is used in emergency response.

Figure 19:
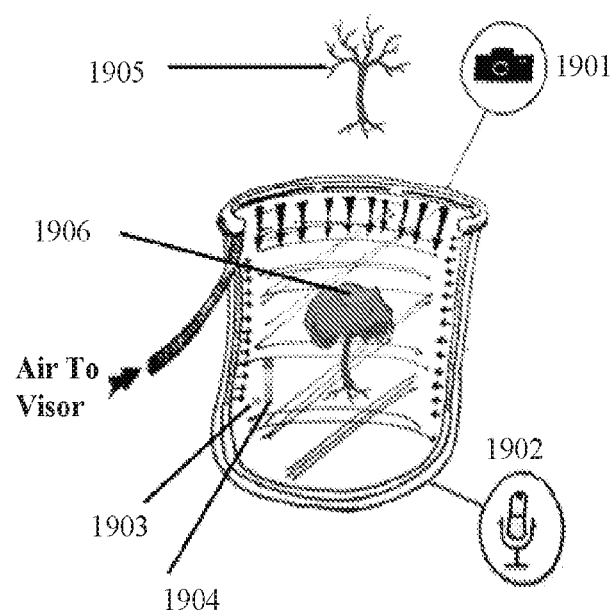
FIG. 19 shows air quality indication and warning, audio and visual data acquisition and processing and augmented reality features.

FIG. 19 shows features of air quality indication and warning, audio and visual data acquisition and processing and augmented reality features. The unit is afforded with video cameras (1901) facing inward and outward as well as audio (1902). (Due to size these features are represented diagrammatically.) Through indicators including and not limited to a heads up display (HUD) and/or LEDs and other display technologies, the internal air quality (1903) and external air quality (1904) are communicated to the user. In this case the user is warned that that the external air quality is deadly. The invention can also augment reality to, on this example, make an image (1905) be more visually pleasing (1906). Other processing such as information about a person one is talking to or weather or the like can of course also be displayed.

Protection Against Radiation Especially Electromagnetic Radiation

The protection pane can preferably and optionally provide protection from electromagnetic radiation, in particular (but not only) UV radiation and excessive visible light, through the appropriate choice of materials which block those wavelengths of electromagnetic radiation. For example, laminate film, desorption technologies and the inclusion of UV absorbers in plastic, among many other approaches and other methods known to one of ordinary skill in the art, can impart UV opaqueness to the protection pane. The protection pane of FIG. 1 (110) is one such material which blocks >95% of UV rays. The protection pane may also be a large liquid crystal panel or similar to allow modulatable tuning of the transmission of light from full-or near full transparency to significant light attenuation. This modulation may be automatic (autodimming or undimming), allowing use in settings where drastic differences in light levels may occur, such as during welding, mining, emergency responder conditions and emergency medical response. The protection pane can also be designed for protection from other radiation sources. By example, frequent exposure to intense infrared (IR) radiation (as frequently occurs, for example, for industrial workers who maintain furnaces or boilers) has been implicated in eye damage. IR blocking materials or coatings may also be added. Similarly, transparent or mostly transparent depositions of lead, or the use of leaded glass, can afford protection from ionizing radiation (alpha, beta and to some extent gamma rays). As the largest surface of the unit, the panel itself may also be a transparent solar panel, extending unit life through solar power.

Monitoring of Pollution Levels

In preferred embodiments, the invention contains pollution sensors chosen to detect the possible contaminants ideally with knowledge of the expected environment. In certain embodiments, one or more pollution sensors detect various pollutants or toxins present in the ambient environment such as gases, fumes, particulate matter, particulate biological toxins, chemicals, allergens, smokes, fumes or toxins in general. Information from the pollution sensor(s) is evaluated and, at a given level, the invention will warn through a sound, light, or any other mechanism and inform the user and/or people in proximity of the device as to the danger. For example, a light visible to the user and others in the vicinity may turn color, likely from green to red, or could start flashing a bright xenon bulb to indicate that the ambient air quality is hazardous. Different signals, such as distinct colors or sounds, might represent different hazards or toxins. In certain embodiments, one or more sensors detect various pollutants or toxins present in the ambient environment (such as gases, fumes, particulate matter, particulate biological toxins, chemicals, allergens, smokes, fumes or toxins in general) and uses that information to modify the air purification process for example by turning on a more thorough air or gas cleaning process, a sterilization system, or a chemical catalysis system which can break down hazardous substances. The invention contemplates a logging and tracking system acquired by the pollution sensors. This logging is to be simultaneously recorded with data from other sensors such as GPS sensors and is logged as a function of time using a time measuring system.

In preferred embodiments, the invention contains sensors to detect when the air purification system to remove contamination is saturated with contaminants. For example, in the use of filters such as HEPA filters, pressure sensors monitor the pressure drop where certain threshold of pressure drop indicates a clogged filter. In certain embodiments, the sensor detecting contamination saturation drives a light or other indicator, which may be audio, visual, vibrational, shock or another suitable signal, to inform the user when to change, update, refill, recharge or clean the air purification system. By example, the pressure drop threshold is triggered and a light goes on to indicate to the user to change a filter. The sensor may alternatively prevent the unit from functioning if the air purification system becomes saturated with contaminants and is not refreshed.

In further embodiments, the protection pane is provided with sensors which detect impacts and their force. Suitable sensors include mechanical shock sensors in general including and not limited to shock, tension, vibration and other sensors using electromechanic, piezoelectric, mechanical or other techniques. In certain embodiment, the protection pane is provided with anti-fog or -hazing measures, such as jets that can clear off the external surface as needed from particulate, anti-fogging coatings and/or warming elements to clear and/or prevent condensation.

Monitoring of Airflow

Airflow monitors may be used to monitor the airflow within the system in various embodiments of the invention. Preferably, due to their potential small size and high accuracy in low flow environments, optical or optomechanical airflow sensors are provided to the system: 1) on the exterior; 2) in various regions of the interior airflow; and 3) on the regions of the protection pane where air exits, for example on bottom and/or edges for top to bottom air flow to monitor the air flow out.

In particular embodiments, the device is provided with airflow sensors which detect wind flow around the user. In a preferred embodiment, such sensors may utilize the protection pane itself in combination with mechanosensors, such as a pressure transducer and other methods known to one of ordinary skill in the art, since the protection pane has the largest surface area of the device. Sensors including and not limited to anemometers and others as described under airflow sensor may be employed; these sensors monitor air flow and turbulence patterns exterior to the device.

In certain embodiments, one or more sensors detect the quality of air supplied for breathing and protection between the user's face and the protection pane; sensors may additionally be present (alone or in combination with the sensors of breathing air) which detect the quality of ambient air. Information from these sensors is processed and used to assure, inform, warn and/or modulate the airflow. By example, higher clean airflow may be necessary if contamination is detected in breathing or ambient air. For example, in instances of clean ambient air, air supply can be reduced or altogether turned off. The device may simultaneously be equipped with machine learning In a particular embodiment, measurements and data collected from other devices in the area detects wind patterns and wind gusts in the immediate area is communicated and used to modulate airflow in anticipation of stronger or weaker than normal external airflow. For example, as wind gusts, wind and air turbulence conditions and/or wind pattern of polluted or clean air are detected and expected to arrive at the user, as detected by external sensors including airflow sensors of the invention and GPS signals of other users in the general area, airflow will be automatically increased immediately before the gust occurs. The device is also equipped with machine learning mechanisms such as machine learning or artificial intelligence that allow it to learn requisite flow to maintain a clean air supply as a function of external pollution levels and turbulence; the invention so modulates the increase in airflow required as a function of wind gust power, utilizing information from contaminants detected in the user's breathable air and external air.

In certain embodiments, the device is fitted with sensors, for example flow sensors, or cameras showing nostril size or movement if the chest or throat or similar, or mechanoelectric or tension sensors on a belt or in clothing, or sensors of nerve impulses and muscle movement and other methods known to one of ordinary skill in the art which allow the device to determine when inhalation and exhalation have occurred, allow the device to measure and monitor inhaled and exhaled breathe and thus allow the device to modulate the air flow, synchronizing airflow to decrease it during exhalation and increase it during inhalation, thus prolonging the time the unit is able to operate from its stored energy. The device may simultaneously be equipped with machine learning or similar such as artificial intelligence or algorithms, allowing it to learn and/or predict patterns of breath, anticipate inhalation and modulate accordingly. As overall airflow is decreased, this modulation has the additional advantage of being less drying to eyes, skin, lips, mouth and body in general. This modulation of airflow is specifically contemplated to be a function of physiological state: airflow regulation and amount will be different for, by example, a person running versus a person sitting. In other embodiments, flow sensors (likely and not necessarily on the exterior edge of the device) determine how much gas is exiting the unit and regulate the output of the air supply system to a constant level, in the preferred embodiment to a level which consistently provides clean air to the user. As with other airflow, the level is anticipated to be adjustable by the user.

In one embodiment, machine learning, algorithms and/or artificial intelligence (AI) are used to determine the necessary airflow as a function of user movement: the device learns from the contaminant sensors in the area between the protection pane and the user's face what airflow is required for a certain desirable level of contaminant air given the motion of the user, for example running, bicycling or playing various sports. The device, in preferred embodiments, also incorporates data from other sensors such as motion sensors to supply the needed level of airflow for a given reduction in air contamination.

Air Quality Control Features

In certain embodiments, the temperature of the supplied air can be measured with a temperature sensor, modulated, controlled, adjusted and/or regulated by heating or cooling systems, for example using various techniques of refrigeration or heating known to one of ordinary skill in the art such as cyclic or non-cyclic refrigeration, thermoelectric refrigeration (Peltier junctions), or by misting with water or other liquids, or by the use of stored heat or cold for example in the form of liquid nitrogen or dry ice, eutectic systems or the other methods known to one of ordinary skill in the art. Heat exchangers and/or temperature regulators, ideally and in the preferred embodiment removable, replaceable, detachable and rechargeable, can be placed typically between the air purification system and the air manifold system which serves to deliver air. As with the housing and air purification system, such a temperature regulation unit or system may have significant weight and is not typically supported by the support system holding the protection pane on the head but rather by a belt, or clip to a belt, fanny pack, backpack or backpack straps, sash support system, etc. which distributes the weight to the user's body.

In further embodiments, the humidity of the supplied air can be measured with a humidity sensor, modulated, controlled or regulated by humidifiers or dehumidifiers, which may work in conjunction with temperature control. This may be accomplished as well with materials which can add or remove water from the air such as desiccants for example those comprised of various types of silica gel, zeolite and/or molecular sieves, among other desiccants, or alternatively materials saturated with water for humidification. Like the air purification system containing the energy storage system and the thermal regulation system described above, is most typically supported by a system such as a belt, or clip to a belt, fanny pack, backpack or backpack straps, sash support system, etc. which distributes the weight to the user's body.

In a particular embodiment, additional gases are supplied to the breathing air, especially oxygen, through an injection system into the airflow provided from a storage system containing the gases to inject. Such injection systems may themselves or may require additional control mechanisms to regulate the amount of gas released. The oxygen level may be monitored with oxygen sensors and adjusted accordingly. Oxygen levels may be measured in the gas phase (holding either the inhaled mix constant, or detecting the exhaled level of oxygen) or be measured in vitro through a measurement device in contact with a person's body (e.g. skin or finger or the like). Other gases may also be used for example a decrease in oxygen content to reset internal clocks and decrease jetlag, gasses used for medical purposes such as anesthetic and analgesic gases such as nitrous oxide or sevoflurane or related, or, in true emergency settings necessitating hibernation, gases such as hydrogen sulfide may be dispensed by the invention at concentrations able to induce hibernation and not death (for $H_2S$ typically in the range of 10-200 ppm).

Lighting and Indicating Features

In certain embodiments, external and/or internal lights controllable manually or automatically provide lighting during conditions of darkness. Such lighting systems may be light emitting diodes (LEDs), FEL lamps, arc lamps including xenon arc lamps, excimer lamps, argon, krypton or xenon flash lamps, carbon button lamp, Super Radiant Light (SRL) sources, cathode ray tubes (CRTs), electroluminescent panels (ELP), cold cathode fluorescent lamps (CCFLs), neon lamps, Geissler and Plucker tubes, solid state lighting (SSL) sources including semiconductor light-emitting diodes (LEDs), organic light-emitting diodes (OLED), or polymer light-emitting diodes (PLED), halogen bulbs and lamps, black lights, carbide lamps, gas lamps, Zirconia lights, electron-stimulated luminescence (ESL) tubes and light sources, gas discharge lamps, low pressure discharge lamps, high pressure discharge lamps, high-intensity discharge lamps, metal halide lamps, mercury lamps, sulfur lamps, ceramic discharge metal halide lamps, hot- and cold-cathode lamps, sodium vapor lamps (high or low pressure), Nernst glowers, plasma lamps, electroless lamps, incandescent or fluorescent lights, laser lamps, lasers, stack lights and many and other methods known to one of ordinary skill in the art. In some embodiments contemplated in cases of precise work such as industrial assembly or medical or surgical use, the lighting systems may be capable of being aimed or directed to provide enhanced lamination (a "spotlight view") to a particular field of view. In such embodiments, there may be more than one lighting system and the lighting system providing a spotlight view may be automatically controlled by the device, which may track the users' eye motions, for example by camera and IR illumination of the eyes among other methods known to one skilled in the art, and light up the specific region where the user is looking. In particular embodiments, various sensors are used to determine a user's mood, or the user enters their mood, or other information is to be communicated or indicated by the device to the user (typically internally with respect to the protection pane) or to others in the vicinity of the user (typically externally with respect to the protection pane) and the device changes color or provides an indication of information via lighting, liquid crystal display (LCD) technologies, electronic paper technologies, plasma display technologies, Digital Light Processing (DPL) displays, cathode ray tube displays, surface-conduction electron-emitter display (SED) or field emission display (FED) technologies and other methods known to one of ordinary skill in the art. Such indicating lights may be in response to any of the data measured or acquired from the sensors contemplated to be available in this invention.

Audio Features

In certain embodiments, audio communication (both sound reception and acoustic broadcasting) means is afforded in particular at least one or more speakers and microphones (or comparable technologies), either internal or external with respect to the protection pane, or both, which may include ear buds or ear covers in those situations where this is desirable, in particular high-noise environments. Audio may be provided by speakers, moving-iron speakers, piezoelectric speakers, magnetostatic magnetostrictive speakers, electrostatic speakers, ribbon and planar magnetic speakers, bending wave speakers, flat panel speakers, Heil air motion transducers, transparent ionic conduction speaker, plasma arc speakers, thermoacoustic speakers, rotary woofers or digital speakers among other methods known to one of ordinary skill in the art. In a further embodiment, noise cancellation especially active noise cancellation is included by the steps of monitoring external noise and broadcasting internally sounds which are 180 degrees out of phase with the external sounds. Other methods known to one of ordinary skill in the art may be used to achieve the same ends.

In particular embodiments, the protection pane itself is used as a speaker or auditory amplifier, by example by attaching piezo transducers or electromechanic coupling to the diaphragm of a speaker, or through the mechanisms of speakers. The embodiment simply uses the protection pane as the diaphragm or membrane of a speaker and its implementation will be understood to one of ordinary skill in the art.

Visual Display and Data Features

In certain embodiments, a camera has been fitted internally (user-facing) and/or externally (viewing in the same direction as the user); the internal face-facing camera affords for, with additional requisite circuitry and communications technology well known to one skilled in the art, visual telecommunications while moving. Similarly, the external camera allows transmission of the view of the user. In a particular embodiment, the protection pane is afforded a means of visual projection or display onto its external as well as internal surfaces, allowing in conjunction with the internal face-facing camera, an image of the user's face (which could be enhanced in appearance) or other information or visual display to be projected on the exterior of the protection pane. Such projection techniques may include liquid crystal display (LCD) technologies, electronic paper technologies, plasma display technologies, Digital Light Processing (DPL) displays, cathode ray tube displays, surface-conduction electron-emitter display (SED), field emission display (FED) technologies, laser scanning technologies (including embedding with transparent phosphors) and heads up display technologies (HUD), though designed to be visible on the exterior rather than interior, among other methods known to one of ordinary skill in the art.

In further embodiments, the protection pane is afforded data display systems such as a heads up display; said data display system can display data obtained from sensors of the device or be interconnected with other external devices such as smart phones or the internet. As known to one skilled in the art, a heads up display consists, in one embodiment, of a projector unit (an optical collimator), a combiner, and a video generation computer in which the projector uses solid state light source (e.g. LEDs among other possibilities), which is modulated by an LCD screen (among other possibilities) to display an image, can use optical waveguides to produce images directly in the combiner or can use a scanning laser to display images and video imagery on a clear transparent medium. Typically a combiner can be a curved, flat, Fresnel or buried Fresnel, arrayed, cascaded prism/mirror, free form TIR, diffractive, holographic waveguide, or holographic light guide combiner or a waveguide, diffractive waveguide, holographic waveguide, polarized waveguide, reflective waveguide, switchable waveguide or a tapered opaque light-guide among other techniques known to one skilled in the art and can employ techniques such as diffraction optics, holographic optics, polarized optics, and reflective optics. It is understood that and other methods known to one of ordinary skill in the art may be employed to the purpose of display of data on the protection pane.

In particular embodiments, the control circuitry is capable of processing and storing data including data from its sensors and external signals, calculating, running applications and receiving and broadcasting information including accessing the internet, Wi-Fi, Bluetooth and other ambient electromagnetic communication channels, and in which the control circuitry can access the sensors and detectors of the device such as cameras, temperature, wind and pollution sensors and other sensors such as GPS location sensors, can interpret such data and present such data to the user through audio, visual or other means. The device is optionally controllable by touching the protection panel, which may be touch sensitive, and/or through voice activated commands, or alternatively through gestures including hand and body gestures.

In a further embodiment, data from the surrounding environment is received (including from sensors of the invention as well as other information such as from ambient electromagnetic signals), analyzed, additional information is accessed from internal or external sources, and the heads up display provides this data to the user, by example through overlay of data about the surroundings onto the viewing surface. A simple example would be directions to travel to a destination avoiding polluted areas, traffic, noise, and other parameters of interest to the user. In another embodiment, data from the external camera is continually analyzed for dangers; when a danger is detected, it is communicated directly and immediately to the user through warnings including sounds, visual clues and/or electrical shocks. A typical danger might be inattention to an oncoming car or an open uncovered hole on a sidewalk. Such systems use the techniques of image processing and recognition optionally combined with the systems of artificial intelligence (AI) and/or machine learning and/or algorithms. It is recognized that other methods known to one of ordinary skill in the art may be employed to the same end of these embodiments.

In yet other embodiments, the external environment is processed and made more visually pleasing before presentation to the user on the internal side of the protection pane through the techniques of augmented reality in which sensory input such as sound, video and graphic input is computer processed to make it more beautiful or aesthetically pleasing. This feature may be combined with a heads up display and, in preferred embodiments, uses similar technologies and/or provides processed audio though speakers, headphones, and the like.

In another embodiment, means of reception and sending such as an antenna or multiple antennae have been afforded for radio/TV/Wi-Fi/GPS/Bluetooth/radio and other signals including wireless, visual and optical signals which can then be stored, manipulated, calculated, processed, interacted with, used and displayed in the device including in and through computational activities, by using electronics and electronic components and other methods well known to one of ordinary skill in the art. It is recognized that the location of the antennae is flexible and may be imbedded within the invention at many places. By sending information to other devices including though the use of wireless signals or coupling to phone systems or internet connections or other means of sending information, the device allows two or more users of the device to communicate visually and auditorially in a bi- or multidirectional fashion (two-way and multi-way conversation are possible for users of the device).

In a further embodiment, the device collects, stores and sends data from its sensors, particularly from pollution sensors in addition to other sensors, detectors and/or cameras, and sensors for atmospheric conditions such as temperature, wind, wind turbulence and flow, humidity, light and UV levels, radiation and electromagnetic radiation, among other useful information such as sensors for detection and sensing of emergency situations (such as explosions) or movement of traffic, and in which these data are used to inform, direct and warn users. Data acquired through these sensors from all users of the device are integrated along with positional data from GPS (and the like) systems as well as Wi-Fi tracking and other systems known to one skilled in the art which provide a location of each individual user of the device into a real-time database of these conditions as a function of location, thus producing a real-time map. This map can be accessed, for example from an internet display site, on a website or portable computational device, a cell phone or smart phone, a GPS display system or alternatively through an internet-connected car or other transportation device, and this map is used by the devices to suggest to the user a best path of travel considering hazard levels (to best avoid them), environmental condition and other data acquired by the device and given where the user wishes to go. For example, based on the combined data from many devices, a user will receive direction to safe areas free of or with minimal exposure to projectiles, particulate and other airborne toxins, gases, UV radiation and fumes; temperatures, humidity, precipitation, wind currents and road or travel conditions can also be considered in the suggestion of a path of travel. These data, including the data from other sensors listed in other paragraphs, are anticipated to be particularly useful in the event of an emergency, suggesting the least dangerous way out of dangerous conditions. Additionally, real-time updating allows for quick modification in the case of rapidly changing conditions, such as in an emergency or emergency response setting. These data can also be used to send warning to other users, either in a bulk, automated format or by sending warnings to specific individuals like friends or doctors; additionally, such warnings can be sent to a specific geographic region. It is expected that additional data may also be input by the user through multiple means including entry by speaking or keyboard, through photographing, through the camera(s) or through other means. It is understood this system may be made most efficient through the use of external computation independent from any one device. It is also understood that the devices may also function independent of external computation, collectively using their own internal processing, storage, calculating and analytical capabilities as a distributed computational network.

In certain embodiments, the device is afforded the ability to project 3D images in addition to surface images (for example in the case of a heads-up display. HUD) through 3D projection techniques such as polarized 3D or autostereoscopic systems, among other methods known to one of ordinary skill in the art. This technology may be part of the display technology of the protection pane display or it may be independent.

Health Monitoring Features

In certain embodiments, sensors (including cameras including the camera recording the face of the user) detecting states of the user's health have been afforded including sensors, which may be either on the wearable device (for example in contact with the head) or on the housing of the air propulsion system, or elsewhere, to monitor the user's temperature, blood pressure, breathing rate, lung capacity, oxygen consumption, $CO_2$ production, heart rate, brain waves, hydration state, skin color, skin conductivity, eye dilatation, eye white color and other physiological states such as electrolyte balance, hematocrit level, levels of electrolytes (including and not limited to sodium (Na+), potassium (K+), chloride (Cl—), bicarbonate ($HCO_3$—), carbon dioxide $CO_2$), levels of blood urea nitrogen (BUN), creatinine, glucose, albumin and total protein, ALP (alkaline phosphatase), ALT (alanine amino transferase), AST (aspartate amino transferase) and bilirubin, levels of various proteins and enzymes and antibodies, nucleic acids, lipids, vitamins, carbohydrates or small molecules or hormones such as epinephrine, melatonin, triiodothyronine, thyroxine, prostaglandins, leukotrienes, prostacyclin, thromboxane, amylin (or Islet Amyloid Polypeptide), anti-Müllerian hormone (or Müllerian inhibiting factor or hormone), adiponectin, adrenocorticotropic hormone (or corticotropin), angiotensinogen and angiotensin, antidiuretic hormone (or vasopressin, arginine vasopressin), atrial-natriuretic peptide (or atriopeptin), brain natriuretic peptide, calcitonin, cholecystokinin, corticotropin-releasing hormone, cortistatin, enkephalin, endothelin, erythropoietin, follicle-stimulating hormone, galanin, gastric inhibitory polypeptide, gastrin, ghrelin, glucagon, glucagon-like peptide-1, gonadotropin-releasing hormone, growth hormone-releasing hormone, hepcidin, human chorionic gonadotropin, human placental lactogen, growth hormone, inhibin, insulin, insulin-like growth factor (or somatomedin), leptin, lipotropin, luteinizing hormone, melanocyte stimulating hormone, motilin, orexin, oxytocin, pancreatic polypeptide, parathyroid hormone, pituitary adenylate cyclase-activating peptide, prolactin, prolactin releasing hormone, relaxin, renin, secretin, somatostatin, thrombopoietin, thyroid-stimulating hormone (or thyrotropin), thyrotropin-releasing hormone, vasoactive intestinal peptide, guanylin, uroguanylin, testosterone, dehydroepiandrosterone, androstenedione, dihydrotestosterone, aldosterone, estradiol, estrone, estriol, cortisol, progesterone, calcitriol (1,25-dihydroxyvitamin D3) and calcidiol (25-hydroxyvitamin D3) and others or signaling molecules); the sensors can also communicate with other internal and external computer and communication systems to warn the user of the device or others of dangerous physiological conditions of the user or to inform the user or others of changing physiological state (either worsening or improving). Sensors worn elsewhere on the body, for example on wristbands or anklets, in shoes, in clothing or on bands somewhere on the body may communicate with the main control circuitry through wireless communication or wired communication. In the case that the user is in a dangerous state of health and potentially unable to move or communicate, the invention is able to alert and call for help through communication channels and use GPS tracking to provide the location of the user. It is also contemplated that these health data can be communicated to a computer or smartphone or the internet or similar and displayed, analyzed and examined. It is further contemplated that the device can make recommendations on health from these data. Finally, it is contemplated that aggregate data from many users of the devices can be analyzed to determine the effect of measured parameters, such as air pollution and airborne toxins (among all other data collected), on health. These data may also be combined with others such as health and/or prescription history to further understand health effects and in the preferred embodiment suggest In particular embodiments, sensors including and not limited to accelerometers, motion sensors, proximity sensors, ambient light sensors, moisture sensors, magnetic sensors, gyroscopes and compasses among others including user input monitor and records user activity such as movement and exercise. This activity is recorded and analyzed, presenting information to the user and suggesting user action. By example, the device may determine that overall health will be improved by with increased exercise or, by example and alternatively, in combination with data acquired about the body and health status, that an optimal level of exercise has been reached. In preferred embodiments, The device then recommends exercise and lifestyle changes to reach a user's health target. Such health targets may include weight loss, training for sports, recovery from illness or injury, etc. It is specifically contemplated that the device, by increasing health and providing data on health and healthy activities and lifestyles, will reduce costs for health insurers and assist health insurers in determining rates, lower rates corresponding to better lifestyle choices including use of the device.

In some embodiments, sensors monitor for emergency conditions. Such sensors include accelerometers, shock sensors, microphones, devices to detect radiation (by example gaseous ionization detectors like Geiger-Müller tubes, ionization chambers or proportional counters, scintillation counters, semiconductor detectors such as silicon, diamond, germanium or cadmium (zinc) telluride detectors, and similar, dosimeters, or electroscopes) and solar radiation including and not limited to UV, and pollution sensors including and not limited to particulate, dust and gas sensors (especially sensors for products of combustion and incomplete combustion such as $CO_2$ and CO and volatile compounds of combustion and other similar indications of fire or combustion or explosion) which can monitor for emergency conditions such as explosions, toxic gas release, nuclear explosions, gunshot, etc. Especially shock sensors may be built into the protection pane or use the protection pane as a receiver of mechanical motion (such as shock and loud noise). All signals from the sensors are continually monitored and analyzed to detect emergency conditions. In the case that such emergency conditions are detected, the device can be configured to send out emergency signals through its integrated electronics, for example by radio signals to connect with the internet or telecommunications systems, which informs, warns and calls for help. The device records exposure constantly and can produce a report upon user demand. In addition, the device supplies information of total exposure to dangers and can compare protected versus unprotected exposure. The device may simultaneously record the results of its sensors for emergency conditions, as with all other sensors, externally by broadcasting or sending these information wirelessly to other locations where information can be separately archived. It is specifically contemplated that the device can couple to smart phones, mobile phones or cell phones as well as Wi-Fi, bluetooth and other wireless connections or networks at all times and that the device would be configurable in an emergency condition of making emergency notifications (such as a 911 call in the United States). The device can also combine information about user health with information from its other sensors and communicate this alone or in combination with an emergency notification.

In particular embodiments, exhaled air is monitor for signatures of health, changes in health, asthma attacks, cancer, levels of medication or drugs such as THC or alcohol, and other exhaled molecules of interest like gases and metabolites, allowing the device to alert the user or people the user deems important to alert such as doctors. Exhaled air may be monitored with sensors such as mass spectrometric detection including Field Asymmetric Ion Mobility Spectrometry (FAIMS), carbon nanotubes with antibodies, chemically surface modified micro electro mechanical system (MEMS) sensors, chemo-mechanical sensing with optical detection and capacitive sensing with electronic detection, calorimetric or catalytic bed, catalytic field-effect sensors (MOSFET), conducting polymer, electrochemical, metal oxides semiconducting (MOS), optical sensors, quartz crystal microbalance and surface acoustic wave sensors among others and other methods known to one of ordinary skill in the art. The data read by such sensors is stored and analyzed, allowing for studies to be carried out and signatures determined which indicate conditions of health and disease. The device records these data simultaneously with health and environmental data.

Medical Care Features

In certain embodiments, the device is fitted with a dosing device such as a sprayer, vaper, atomizer, vaporizer, inhaler or electrospray device and other methods known to one of ordinary skill in the art which can administer medication to the space between the protection pane and the user's face. The device may deliver a wide variety of medications including antipyretics, analgesics, antimalarial drugs, antibiotics, antiseptics, mood stabilizers, hormones and hormone replacements including contraceptives, stimulants, tranquilizers, statins, amphetamines, anabolic steroids, anesthetics, antacids, anticoagulants, antidepressants, antidotes, antihistamines, anti-inflammatories, antiretrovirals, barbiturates, beta-blockers, contraceptives, decongestants, depressants, emetics, expectorants, hypnotics, laxatives, vaccines, vitamins and multivitamins, narcotics, opiates, painkillers, prophylactics, purgatives, relaxants, sedatives, steroids, supplements, suppressants, tinctures and herbal extracts, tonics, tranquilizers among others. Medications are ideally provided directly in front of the user's mouth and nose and may be optimally delivered through a third air system such as a tube. The device can measure and titrate the amount, timing of dose and kind of medication in response to data it collects from the user's body and from its internal and external sensors including sensors for emergency conditions. Depending on configuration, medication can be administered manually or automatically to treat a health condition detected by the device, or may be administered in an emergency situation. For example, bronchodilators might be administered during an asthma attack or antibiotics might be administered at the detection of gunshot. Additional, coupled with the sensors of exhaled air, the device can be used to deliver and monitor anesthetic in emergency or remote medicine circumstances. In addition, this delivery system can be used to treat addiction, such as nicotine addiction, by microdosing decreasing levels of nicotine or other addictive drug. It can also improve performance by microdosing compounds like caffeine, while monitoring the total does.

The foregoing descriptions of specific embodiments of the present application have been presented for purposes of illustration and description. They are not intended to be exhaustive or to limit the application and method of use to the precise forms disclosed. Obviously many modifications and variations are possible in light of the above teaching. It is understood that various omissions or substitutions of equivalents are contemplated as circumstance may suggest or render expedient, but is intended to cover the application or implementation without departing from the spirit or scope of the claims of the present application.

What is claimed is:

1. A device for delivery of purified air to a face of a subject in need thereof, comprising:

an air purification system, wherein said air purification system has an attachment via an enclosed space to a manifold air delivery system;

a support system that supports said manifold air supply system and connects said manifold air supply system to a protection pane, wherein the protection pane has an edge which is in contact with contaminated air outside the protection pane;

a first air supply system and a second air supply system that are connected to said protection pane;

a plurality of apertures in said first air supply system that are orientated to direct airflow over said face of said subject when said protection pane is positioned to deliver air to said subject;

a plurality of apertures in said second air supply system that are orientated to direct airflow over said face of said subject when said protection pane is positioned to deliver air to said subject;

and wherein said apertures of second air supply system are oriented to direct airflow in an enclosing direction to said airflow from said apertures of said first air supply system;

and further wherein said support system, said manifold air supply system, said protection pane and said first air supply system and said second air supply system are integrated to form a single unit., wherein said apertures of said second air supply system are configured to supply a directed airflow that is parallel to said face of said subject, and wherein said second air supply system is configured to at least partially encircle said face of said subject; and said directed airflow from said first air supply system is a majority of air received from said air purification system; and wherein said first air supply system and said second air supply system are positioned upon said protection pane, wherein said positions of said first and second air supply system do not overlap upon said protection pane, and wherein said plurality of apertures of said second air supply system are part of the protection pane and positioned at the edge of the protection pane so that the airflow within the system seals against contaminated air in absence of sealing skirts attached to the edges of the protection pane or sealing of the edges of the protection pane against the user's body.

2. The device of claim 1, wherein the device further comprises a pollution sensor.

3. The device of claim 2, wherein the pollution sensor communicates a warning to the subject that pollution levels are elevated above a threshold level.

4. The device of claim 3, wherein the air purification system is modified to respond to the detection of elevated pollution levels.

5. The device of claim 1, wherein the device comprises a wireless communication unit, wherein the wireless communication unit is in communication with other devices worn by subjects.

6. The device of claim 5, wherein the device receives communications from other devices regarding pollution, traffic or heat.

7. The device of claim 1, wherein the protection pane comprises a liquid crystal panel, wherein the liquid crystal panel permits modulatable tuning of the transmission of light from full—or near full transparency to significant light attenuation.

8. The device of claim 1, wherein the device is attached to a vehicle, wherein the device is supported by the vehicle, and further wherein the occupant of the vehicle receives the air flow directed by the device.

9. The device of claim 1, wherein the device comprises an injection system into the airflow provided from a storage system containing additional gases to inject into the airflow.

10. The device of claim 1, wherein the device comprises external and/or internal lights controllable manually or automatically to provide lighting during conditions of darkness.

11. The device of claim 1, wherein the device comprises at least one or more speakers and microphones, wherein speakers or microphones are either internal or external with respect to the protection pane, or both.

12. The device of claim 1, wherein the device comprises ear buds or ear covers.

13. The device of claim 1, wherein the device comprises airflow sensors which detect wind flow around the user.

14. The device of claim 1, wherein the device comprises a camera fitted internally, wherein the internal camera is user-facing, and/or externally, wherein the external camera is facing the same direction as the user's viewpoint.

15. The device of claim 1, wherein the device comprises health sensors selected from the group comprising sensors for the user's temperature, blood pressure, breathing rate, lung capacity, oxygen consumption, $CO_2$ production, heart rate, brain waves, hydration state, skin color, skin conductivity, eye dilation, or eye white color.

16. A system for providing air and protection from environmental hazards to a subject in need thereof, comprising:

a housing having an air intake and an air exit;

an air purification system that receives air that has passed through said air intake of said housing; an air delivery system that delivers air that has passed through said air purification system and through said air exit of said housing;

a manifold air delivery system that receives air from said air delivery system;

a support system that supports said manifold air supply system and connects said manifold air supply system to a protection pane, wherein the protection pane has an edge which is in contact with contaminated air outside the protection pane;

a first air supply system and a second air supply system that are connected to said protection pane;

said first air supply system is configured to receive air from said manifold air delivery system, wherein said first air supply system comprises a plurality of apertures that are orientated to direct airflow in a space between said protection pane and a face of said subject, wherein said protection pane is positioned to deliver air to said subject;

said second air supply system is configured to receive air from said manifold air delivery system, wherein said second air supply system comprises a plurality of apertures that are orientated to direct airflow in said space between said protection pane and said face of said subject, wherein said protection pane is positioned to deliver air to said subject; and wherein said plurality of apertures of said second air supply system are oriented to direct airflow in an enclosing direction to said airflow from said apertures of said first air supply system; and further wherein said support system, said manifold air supply system, said protection pane and said first air supply system and said second air supply system are integrated to form a single unit, wherein said apertures of said second air supply system are configured to supply a directed airflow that is parallel to said face of said subject, and wherein said second air supply system is configured to at least partially encircle said face of said subject: and said directed airflow from said first air supply system is a majority of air received from said air purification system; and wherein said first air supply system and said second air supply system are positioned upon said protection pane, wherein said positions of said first and second air supply system do not overlap upon said protection pane, and wherein said plurality of apertures of said second air supply system are part of the protection pane and positioned at the edge of the protection pane so that the airflow within the system seals against contaminated air in absence of sealing skirts attached to the edges of the protection pane or sealing of the edges of the protection pane against the user's body.

17. The system of claim 16, wherein said housing has an interior that comprises an air propulsion system, an energy storage system or an energy generation system, and control circuitry that controls said air propulsion system, said energy storage system or said energy generation system.

18. The system of claim 17, wherein said air purification system is positioned within said interior of said housing.

19. A method for providing air and protection from environmental hazards to a subject in need thereof, comprising:

pulling air through an air intake of a housing;

passing said air through an air purification system;

expelling said air through an air exit of said housing and into a flexible air delivery system; feeding air into a manifold air delivery system through said flexible air delivery system;

supporting said manifold air supply system via a support system that connects said manifold air supply system to a protection pane, wherein the protection pane has an edge which is in contact with contaminated air outside the protection pane;

connecting a first air supply system and second air supply system to said protection pane;

delivering air through said manifold air delivery system into said first air supply system and said second air supply system;

positioning said first air supply system and said second air supply system upon a protection pane, wherein said positions of said first and second air supply system do not overlap upon said protection pane;

integrating said first air supply system and said second air supply system into said positions on said protection pane;

placing said protection pane in front of a face of a subject;

directing airflow from said first air supply system over said face of said subject when said protection pane is in front of said face of said subject, wherein a plurality of apertures in said first air supply system controls said direction of said airflow from said first air supply system;

directing airflow from said second air supply system over said face of said subject when said protection pane is positioned to deliver air to said subject, wherein a plurality of apertures in said second air supply system controls said direction of said airflow from said second air supply system;

orientating said apertures of said first and second air supply systems so that said direction of airflow from said second air supply system is in an enclosing direction to said direction of airflow from said first air supply system when said protection pane is positioned to deliver air to said subject, wherein said apertures of said second air supply system are configured to supply a directed airflow that is parallel to said face of said subject, and wherein said second air supply system is configured to at least partially encircle said face of said subject: and said directed airflow from said first air supply system is a majority of air received from said air purification system, and wherein said plurality of apertures of said second air supply system are part of the protection pane and positioned at the edge of the protection pane so that the airflow within the system seals against contaminated air in absence of sealing skirts attached to the edges of the protection pane or sealing of the edges of the protection pane against the user's body.

* * * * *